US009096505B2

(12) United States Patent
Robertson et al.

(10) Patent No.: US 9,096,505 B2
(45) Date of Patent: Aug. 4, 2015

(54) ANTI-CANCER COMPOSITIONS AND METHODS

(71) Applicant: The Penn State Research Foundation, University Park, PA (US)

(72) Inventors: Gavin P. Robertson, Hummelstown, PA (US); Arati K. Sharma, Hummelstown, PA (US); Arun K. Sharma, Hummelstown, PA (US); Shantu G. Amin, Union City, NJ (US); Dhimant H. Desai, Mechanicsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/785,552

(22) Filed: Mar. 5, 2013

(65) Prior Publication Data
US 2013/0184339 A1 Jul. 18, 2013

Related U.S. Application Data

(63) Continuation of application No. 12/102,629, filed on Apr. 14, 2008.

(60) Provisional application No. 60/911,565, filed on Apr. 13, 2007, provisional application No. 60/959,554, filed on Jul. 13, 2007.

(51) Int. Cl.
*A61K 31/21* (2006.01)
*A61K 31/095* (2006.01)
*C07C 391/00* (2006.01)
*A61K 45/06* (2006.01)
*C07C 251/00* (2006.01)

(52) U.S. Cl.
CPC ............. *C07C 391/00* (2013.01); *A61K 31/095* (2013.01); *A61K 31/21* (2013.01); *A61K 45/06* (2013.01); *C07C 251/00* (2013.01)

(58) Field of Classification Search
CPC .............................. A61K 31/21; A61K 31/095
See application file for complete search history.

(56) References Cited

U.S. PATENT DOCUMENTS

| | | | |
|---|---|---|---|
| 4,988,517 A | 1/1991 | El-Bayoumy et al. | |
| 5,093,351 A | 3/1992 | Batt | |
| 5,114,969 A | 5/1992 | Chung et al. | |
| 5,231,209 A | 7/1993 | Chung et al. | |
| 5,411,986 A | 5/1995 | Cho et al. | |
| 5,648,097 A | 7/1997 | Nuwayser | |
| 5,929,063 A | 7/1999 | Southan et al. | |
| 5,985,917 A | 11/1999 | Southan et al. | |
| 6,166,003 A | 12/2000 | Lam | |
| 6,465,512 B2 | 10/2002 | Nakamura et al. | |
| 6,511,970 B1 | 1/2003 | Rodriguez | |
| 6,630,486 B1 | 10/2003 | Royer | |
| 6,703,524 B2 | 3/2004 | Lam et al. | |
| 6,737,441 B2 | 5/2004 | Fahey | |
| 7,087,639 B2 | 8/2006 | Lam et al. | |
| 7,314,929 B2 | 1/2008 | Lam et al. | |
| 2002/0165215 A1 | 11/2002 | Lam et al. | |
| 2004/0158079 A1 | 8/2004 | Lam et al. | |
| 2005/0267060 A1* | 12/2005 | Robertson et al. | ............... 514/44 |

FOREIGN PATENT DOCUMENTS

EP 0750911 1/1997

OTHER PUBLICATIONS

Chiao, J. et al., Ingestion of an Isothiocyanate Metabolite from Cruciferous Vegetables Inhibits Growth of Human Prostate Cancer Cell Xenografts by Apoptosis and Cell Cycle Arrest, *Carcinogenesis*, 25(8):1403-1408, 2004.
Conaway, C. et al., Inhibition of Rat Liver Cytochrome P450 Isozymes by Isothiocyanates and Their Conjugates: a Structure-Activity Relationship Study, *Carcinogenesis*, 17(11):2423-2427, 1996.
Conaway, C. et al., Isothiocyanates as Cancer Chemopreventative Agents: Their Biological Activities and Metabolism in Rodents and Humans, *Current Drug Metabolism*, 3:233-255, 2002.
Jiao, D. et al., Structure-Activity Relationships of Isothiocyanates as Mechanism-based Inhibitors of 4-(Methylnitrosamino)-1-(3-pyridyl)-1-butanone-induced Lung Tumorigenesis in A/J Mice, *Cancer Research*, 54:4327-4333, Aug. 15, 1994.
Misiewicz, M. et al., Sulforaphane and 2-oxyhexyl isothiocyanate Induce Cell Growth Arrest and Apoptosis in L-1210 Leukemia and ME-18 Melanoma Cells, *Oncol. Rep.*, 10(6):2045-2050, 2003 (Absract).
Morse, M. et al., Structure-Activity Relationships for Inhibition of 4-(Methylnitrosamino)-1-(3-pyridyl)-1-butanone Lung Tumorigenesis by Arylalkyl Isothiocyanates in A/J Mice, *Cancer Research*, 51:1846-1850, Apr. 1, 1991.
Sasaki, T. et al., Effects of Isothiocyanates on Growth and Metastaticity of B16-F10 Melanoma Cells, *Nutr. Cancer*, 33(1):76-81, 1999 (Absract).
Stoner, G. et al., Isothiocyanates and Freeze-Dried Strawberries as Inhibitors of Esophageal Cancer, *Toxicological Sciences*, 52 (Supp): 95-100, 1999.
Xiao, D. et al., Allyl Isothiocyanate, a Constituent of Cruciferous Vegetables, Inhibits Proliferation of Human Prostate Cancer Cells by Causing G2/M Arrest and Inducing Apoptosis, *Carcinogenesis*, 24(5):891-897, 2003.

(Continued)

*Primary Examiner* — Samira Jean-Louis
(74) *Attorney, Agent, or Firm* — Gifford, Krass, Sprinkle, Anderson & Citkowski, P.C.

(57) ABSTRACT

Anti-cancer compositions and methods are described including one or more isothiocyanates and/or isoselenocyanates. Methods of treating a subject are provided according to embodiments of the present invention which include administering a therapeutically effective amount of a composition including an isothiocyanate and/or isoselenocyanate to a subject having a condition characterized by Akt dysregulation. Administering a therapeutically effective amount of a composition including an isothiocyanate and/or isoselenocyanate to a subject detectably increases apoptosis and/or decreases proliferation of cancer cells, particularly cancer cells characterized by Akt dysregulation.

8 Claims, 19 Drawing Sheets

(56) References Cited

OTHER PUBLICATIONS

Tanaka, T. et al., Suppressing Effects of Dietary Supplementation of the Organoselenium 1,4-Phenylenebis(methylene)selenocyanate and the Citrus Antioxidant Auroptene on Lung Metastasis of Melanoma Cells in Mice, *Cancer Research*, 60: 3713-3716, Jul. 15, 2000.

Reddy, B. et al., Chemoprevention of Colon Cancer by Organoselenium Compounds and Impact of High- or Low-Fat Diets, *Journal of the National Cencer Institute*, 89(7): 506-518. Apr. 2, 1997.

Rao, C. et al., Chemoprevention of Colon Cancer by a Glutathione Conjugate of 1,4- Phenylene*bis*(methylene)selenocyanate, a Novel Organoselenium Compound with Low Toxicity, *Cancer Research*, 61: 3647-3652, May 1, 2001.

Reddy, B. et al., Chemoprevention of Colon Cancer by the Synthetic Organoselenium Compound 1,4-Phenylene*bis*(methylene)selenocyanate,*Cancer Research*, 52: 5635-3540, Oct 15, 1992.

Conaway, C. et al., Phenethyl Isothiocyanate and Sulforaphane and their N-Acetylcysteine Conjugates Inhibit Malignant Progression of Lung Adenomas Induced by Tobacco Carcinogens in A/J Mice, *Cancer Research*, 65(1): 8548-8557, Sep. 15, 2005.

Jiao, D. et al., Chemopreventive activity of thiol conjugates of isothiocyanates for lung tumorigenesis, *Carcinogenesis*, 18(11):2143-2147, 1997.

West, K. et al., Rapid Akt activation by nicotine and a tobacco carcinogen modulates the phenotype of normal human airway epithelial cells, *The Journal of Clinical Investigation*, 111(1): 81-90, Jan. 2003.

El-Bayoumy, K. et al., Cancer Chemoprevention by Garlic and Garlic-Containing Sulfur and Selenium Compounds, *The Journal of Nutrition*, pp. 864S-869S, 2006.

Garvey, E. et al., Potent and Selective Inhibition of Human Nitric Oxide Syntheses, *The Journal of Biological Chemistry*, 269(43): 26669-26676, Oct. 28, 1994.

Fernandez-Bolanos, J. et al., Synthesis of O-unprotected glycosyl selenoureas. A New access to bicyclic sugar isoureas, *Tetrahedron Letters*, 45: 4081-4084, 2004.

Datta, S. et al., Cellular survival: a play in three Akts, *Genes & Development*, 13: 2905-2927, 1999.

Fayard, E. et al., Protein Kinase B/Akt at a Glance, *Journal of Cell Science*, 118(24): 5675-5678, Dec. 15, 2005.

Testa, J. et al., AKT plays a central role in tumorigenesis, PNAS, 98(20): 10983-10985, Sep. 25, 2001.

Stahl JM, et al., Deregulated Akt3 activity promotes development of malignant melanoma. *Cancer Research*, 64:7002-10, Oct. 1, 2004.

Stahl JM, et al., Loss of PTEN Promotes Tumor Development in Malignant Melanoma, *Cancer Research*, 63:2881-90, Jun. 1, 2003.

Marani, A. et al., New Synthesis Method of Polythiophenes, *Iranian Jouranl of Polymer Science and Technology*, 3(1): 2-12, Jan. 1994.

Rao, C. et al., Chemoprevention of colonic aberrant crypt foci by an inducible nitric oxide synthase-selective inhibitor, *Carcinogenesis*, 20(4): 1-644, 1999.

Crowell, J. et al., Is Inducible Nitric Oxide Synthase a Target for Chemoprevention?, *Molecular Cancer Therapeutics*, 2: 815-823, Aug. 2003.

Chen, T. et al., Chemopreventive Effects of a Selective Nitric Oxide Synthase Inhibitor on Carcinogen-Induced Rate Esophageal Tumorigenesis, *Cancer Research*, : 3714-3717, May 15, 2004.

Ip, C., Comprison of selenium and sulfur analogs in cancer prevention, *Carcinogenesis*, 13(7): 1167-70, Jul. 1992.

Das, R., et al., Amelioration of benzo (*a*) pyrene-induced lung carcinogenesis in strain A mice by diphenylmethyl selenocyanate, *Experimental and Toxicologic Pathology*, 58: 351-360, 2007.

Helmbach, H. et at, Drug-Resistance in Human Melanoma, *International Journal of Cancer*, 93: 617-622, 2001.

Markovic, S., et al., Malignant Melanoma in the 21st Century, Part 1: Epidemiology, Risk Factors, Screening, Prevention, and Diagnosis, *Mayo Clinic Proceedings*, 82(3): 364-380, Mar. 2007.

Amiri, K. et al., Augmenting Chemosensitivity of Malignant Melanoma Tumors via Proteasome Inhibition: Implication for Bortezomib (VELCADE, PS-341) as a Therapeutic Agent for Malignant Melanoma, *Cancer Research*, 64:4912-4918, 2004.

Madhunapantula, S. et al., PRAS0 Deregulates Apoptosis in Malignant Melanoma, *Cancer Research*, 67: 3626-36, 2004.

Zhang, Y., et al., Anticarcinogenic activities of sulforaphane and structurally related synthetic norbornyl isothiocyanates, *Proceedings of National Academy of Sciences of the USA*, 91: 3147-50, 1994.

Zhang, Y. et al., Vegetable-derived isothiocyanates: anti-proliferative activity and mechanism of action, *Proceedings of the Nutrition Society*, 65: 68-75, 2006.

Miyoshi, N. et al., A Link Between Benzyl Isothiocyanate-Induced Cell Cycle Arrest and Apoptosis: Involvement of Mitogen-Activated Protein Kinases in the Bcl-2 Phosphorylation, *Cancer Research*, 64: 2134-2142, Mar. 15, 2004.

Yang, L. et al., Akt/Protein Kinase B Signaling Inhibitor-2, a Selective Small Molecule Inhibitor of Akt Signaling with Antitumor Activity in Cancer Cells Overexpressing Akt, *Cancer Research*, 64: 4394-4399, Jul. 1, 2004.

Karst, A. et al., Role of p53 Up-regulated Modulator of Apoptosis and Phosphorylated Akt in Melanoma Cell Growth, Apoptosis, and Patient Survival, *Cancer Research*, 66(18): 9221-9226, Sep. 15, 2006.

Hu, H. et al., PKB/AKT and ERK regulation of caspase-mediated apoptosis by methylseleninic acid in LNCaP prostate cancer cells, *Carcinogenesis*, 26(8): 1374-1381, 2005.

Unni, E. et al., Se-methylselenocysteine inhibits phosphatidylinositol 3-kinase activity of mouse mammory epithelial tumor cells in vitro, *Breast Cancer Research*, 7: R699-R707, 2005.

Krishan, A., Rapid flow cytofluorometric analysis of mammalian cell cycle by propidium iodide staining, *Journal of Cell Biology*, 66: 188-193, 1975.

Hecht, S., Chemoprevention by Isothiocyanates, *Cancer Chemopreventative*, 1: 21-35, 1995.

Salvucci, O. et al., Antiapoptotic Role of Endogenous Nitric Oxide in Human Melanoma Cells, *Cancer Research*, 61: 318-326, Jan. 1, 2001.

Ekmekcioglu, S. et al., Inducible Nitric Oxide Synthase and Nitrotyrosine in Human Metastatic Melanoma Tumors Correlate with Poor Survival, *Clinical Cancer Research*, 6: 4768-4775, Dec. 2000.

Ekmekcioglu, S. et al., Tumor iNOS predicts poor survival for stage III melanoma patients, *International Journal of Cancer*, 119: 861-866, 2006.

Madhunapantula, S. et al., Is B-Raf a Good Therapeutic Target for Melanoma and Other Malignancies?, *Cancer Research*, 68(1): 5-8, Jan. 1, 2008.

Lang, J. et al., Absence of Exon 15 BRAF Germline Mutations in Familial Melanoma, *Human Mutation*, 21: 327-330, 2003.

Davies, H. et al., Mutations of the BRAF Gene in Human Cancer, *Nature*, 417: 949-954, Jun. 27, 2002.

Cheung, M. et al., Akt and Mutant $^{V600}$EB-Raf Cooperate to Prormote Early Melanoma Development, *Cancer Research*, 68(9): 3429-3439, May 1, 2008.

Sharma, A. et al., Target Mitogen-Activated Protein Kinase/Extracellular Signal-Regulated Kinase Kinase in the Mutant (V600E) B-Raf Signaling Cascade Effectively Inhibits Melanoma Lung Metastases, *Cancer Research*, 66(16): 8200-09, Aug. 15, 2006.

Sharma, A. et al., Mutant $^{V599E}$ B-Raf Regulates Growth and Vascular Development of Malignant Melanoma Tumors, *Cancer Research*, 65(6): 2412-2421, Mar. 15, 2005.

Jemal, A. et al., Cancer Statistics 2002, *Cancer Journal for Clinicians*, 52: 23-47, 2002.

Grossman D, et al., Drug resistance in melanoma: mechanisms, apoptosis, and new potential therapeutic targets. Cancer & Metastasis Reviews 2001; 20:3-11.

Gray-Schopfer V, et al., Melanoma biology and new targeted therapy. Nature 2007;445:851-857.

Brazil DP, et al., Ten years of protein kinase B signalling: a hard Akt to follow. Trends Biochem Sci 2001;26:657-64.

Nicholson KM, The protein kinase B/Akt signalling pathway in human malignancy. Cell Signal 2002;14:381-95.

(56) References Cited

OTHER PUBLICATIONS

Keum YS, et al., Chemoprevention by isothiocyanates and their underlying molecular signaling mechanisms. Mutat Res 2004;555:191-202.

Zhang Y., Cancer-preventive isothiocyanates: measurement of human exposure and mechanism of action. Mutat Res 2004;555:173-90.

Ji Y, et al., Pharmacokinetics of dietary phenethyl isothiocyanate in rats. Pharm Res 2005;22:1658-66.

Robertson, G.P., Functional and therapeutic significance of Akt deregulation in malignant melanoma, Cancer Metastasis Rev., 2005, 24:273-85.

Rao, C.V., Nitric oxide signaling in colon cancer chemoprevention, Mutat. Res., 2004;555:107-19.

Misko, T.P. et al., Selective inhibition of the inducible nitric oxide synthase by aminoguanidine, Eur J. Pharmacol., 1993;233:119-25.

Tunctan B, et al., Inhibition of extracellular signal-regulated kinase (ERK1/2) activity reverses endotoxin-induced hypotension via decreased nitric oxide production in rats, Pharmacol. Res., 2007, 56:56-64.

Michaloglou, C. et al., BRAFE600-associated senescence-like cell cycle arrest of human naevi, *Nature*, 436:720-4, 2005.

Dhomen, N. et al., Oncogenic Braf induces melanocyte senescence and melanoma in mice, Cancer Cell, 2009, 2009, 15, 294-303.

Jakubikova, J. et al., Role of PI3K/Akt and MEK/ERK signaling pathways in sulforaphane- and erucin-induced phase II enzymes and MRP2 transcription, G2/M arrest and cell death in Caco-2 cells, Biochemical Pharmacology, 69(11): 1543-52, Jun. 1, 2005.

Xu, K. et al., Studies on the mechanism of the inhibition of human leukaemia cell growth by dietary isothiocyanates and their cysteine adducts in vitro, Biochemical Pharmacology, 60(2): 221-31, Jul. 15, 2000.

Serrone L, et al., The chemoresistance of human malignant melanoma: and update, *Melanoma Research*, 9: 51-58, 1999.

Reinhold U, et al., Serum selenium levels in patients with malignant melanoma, *Acta Derm Veroel*, 69:132-136, 1989.

Feun L, et al., A phase II trial of tricyclic nucleoside phosphate in patients with advanced squamous cell carcinoma of the cervix, *American Journal of Clinical Oncology*, 16(6):506-508, 1993.

Massi D, et al., Inducible nitric oxide synthase expression in benign and malignant cutaneous melanocytic lesions, *Journal of Pathology*, 194: 194-200, 2001.

Zheng M, et al., WP760, a melanoma selective drug, *Cancer Chemother Pharmacol*, 60: 625-633, 2007.

Ellerhorst JA, et al., Regulation of iNOS by the p44/42 mitogen-activated protein kinase pathway in human melanoma, *Oncogene*, 25: 3956-3962, 2006.

Manesh C, et al., Effect of naturally occurring allyl and phenyl isothiocyanates in the inhibition of experimental pulmonary metastasis induced by B16F-10 melnoma cells, *Fitoterapia*, 74:355-363, 2003.

Jakubikova J, et al., Effects of MEK1 and PI3K inhibitors on allyl-, benzyl- and phenylethyl-isothiocyanate-induced $G_2/M$ arrest and cell death in Caco-2 cells, *International Journal of Oncology*, 27(5): 1449-1458, 2005.

Morse M, et al., Effects of alkyl chain length on the inhibition of NNK-induced lung neoplasia in A/J mice by arylalkyl isothiocyanates, *Carcinogenesis*, 10(9):1757-1759, 1989.

Bandura, L. et al., Differential effects of selenite and selenate on human melanocytes, keratinocytes, and melanoma cells, *Biochemistry and Cell Biology*, 83: 196-211, 2005.

Brigelius-Flohe, R., Selenium Comppunds and Selenoproteins in Cancer, *Chemistry & Biodiversity*, 5:389-395, 2008.

S. Madhunapantula et al., Development of a novel iNOS inhibitor that retards melanoma metastasis, Abstract online, Mar. 12, 2007.

S. Madhunapantula et al., A Novel Selenium Analog of the iNOS Inhibitor Retards Melanoma—Tumor Development, 2007 AACR Annual Meeting, Los Angeles, CA, Apr. 15, 2007.

A. Sharma et al., Identification of small molecule inhibitors that target Akt3 signaling in melanoma, Abstract online, Mar. 12, 2007.

A. Sharma et al., Identification of small molecule inhibitors that target Akt3 signaling in melanoma, 2007 AACR Annual Meeting, Los Angeles, CA, Apr. 16, 2007.

D. Desai et al., Chemopreventive and therapeutic efficacy of a new selective nitric oxide synthase inhibitor on melanoma lung metastasis, Abstract online, Mar. 12, 2007.

A. Sharma et al., Synthesis and biological activity comparison of isoselenocyanates with isothiocyanate present in cruciferous vegetables, Abstract online, Mar. 12, 2007.

A. Sharma et al., Synthesis and biological activity comparison of isoselenocyanates with isothiocyanate present in cruciferous vegetables, 2007 AACR Annual Meeting, Los Angeles, CA, Apr. 16, 2007.

Michaloglou, C. et al., BRAFE600 in benign and malignant human tumours, *Oncogene*, 27: 877-95, 2008.

* cited by examiner

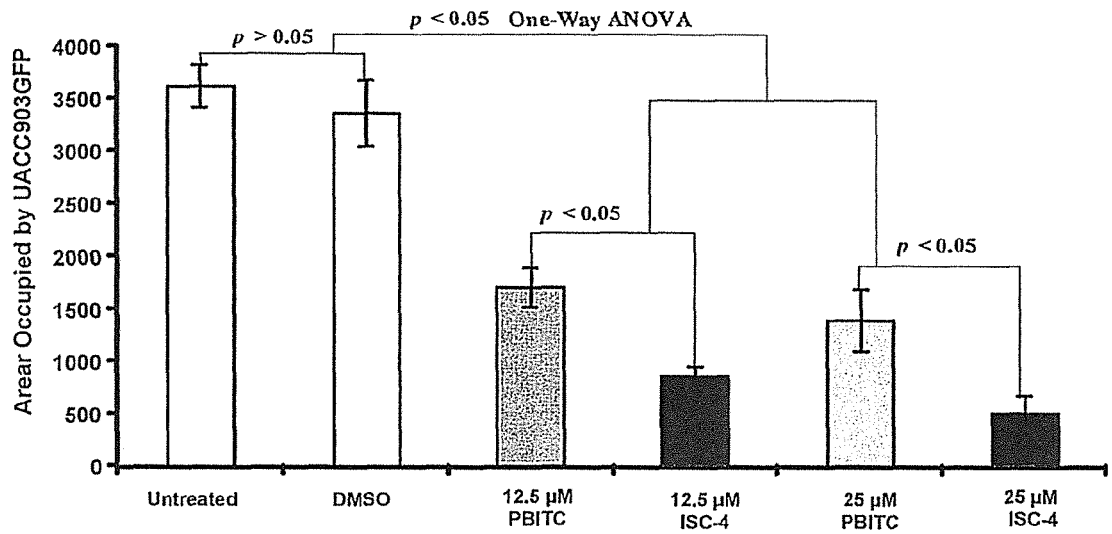
Figure 19
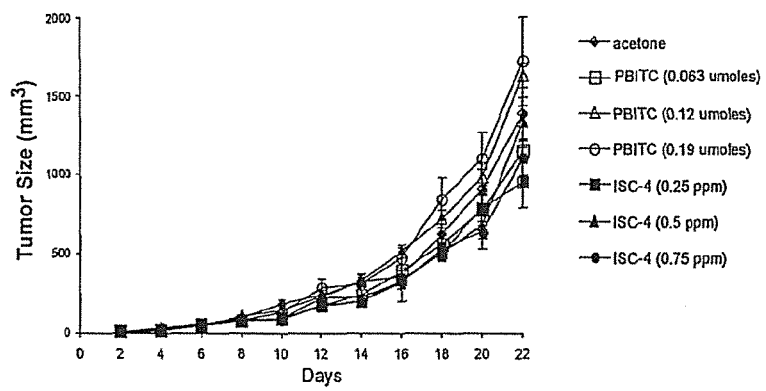
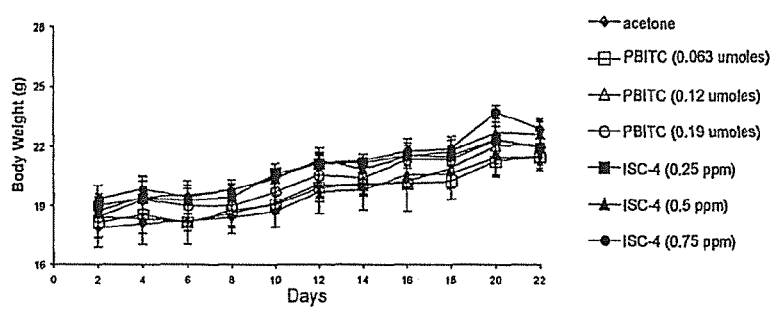
Figure 20

ANTI-CANCER COMPOSITIONS AND METHODS

REFERENCE TO RELATED APPLICATIONS

This application is a continuation of U.S. patent application Ser. No. 12/102,629, filed Apr. 14, 2008, which claims priority from U.S. Provisional Patent Application Ser. Nos. 60/911,565, filed Apr. 13, 2007 and 60/959,554, filed Jul. 13, 2007, the entire content of all of which is incorporated herein by reference.

GOVERNMENT SPONSORSHIP

The invention was made with government support under Grant Nos. CB056603, CA127892, CA136667, CA128033 and HHSN261200566003C awarded by The National Institutes of Health. The Government has certain rights in the invention.

FIELD OF THE INVENTION

The present invention relates generally to anti-cancer compositions and methods. In specific embodiments, the present invention relates to compositions including one or more isothiocyanates and/or isoselenocyanates, methods for treatment and/or prevention of pathological conditions in a subject using one or more isothiocyanates and/or isoselenocyanates and methods for synthesis of particular isoselenocyanates.

BACKGROUND OF THE INVENTION

In spite of recent medical progress, cancer continues to be one of the most common and deadly diseases. Elucidation of biochemical pathways involved in development and progression of various cancers is important to identify potential anti-cancer treatments as well as to develop agents effective to regulate such pathways in other aspects of health and disease.

A particular cancer, melanoma, is the most deadly form of skin cancer due to its high metastatic potential. Akt3 and downstream PRAS40 are part of a key signaling cascade activated in ~70% of melanomas. Akt3 functions to reduce cellular apoptosis in early melanomas, thereby promoting development of this disease. Compositions and methods are required to inhibit the Akt pathway and inhibit abnormal cell survival and proliferation.

SUMMARY OF THE INVENTION

Compositions including an isoselenocyanate having the structural formula R—$(CH_2)_n$—N=C=Se, where n is an integer in the range of 1-8, inclusive, and where R is selected from the group consisting of: an aromatic group and a non-aromatic organic group are described herein.

In embodiments of the present invention, a composition including an isoselenocyanate having the structural formula:

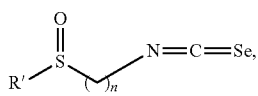

where R' is a substituted or unsubstituted, branched or straight chain, lower alkyl group, and where n is an integer in the range of 3-8, inclusive is provided along with methods of synthesis and use of such compositions. In particular embodiments, R' is $CH_3$.

Embodiments of compositions of the present invention include an isoselenocyanate having the structural formula:

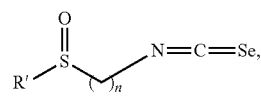

where R' is a substituted or unsubstituted, branched or straight chain, lower alkyl group, and where n is an integer in the range of 3-8, inclusive. In particular embodiments, R' is $CH_3$ and n is 4.

Methods for synthesis of an isoselenocyanate having the structural formula: R—$(CH_2)_n$—N=C=Se, where n is an integer in the range of 1-8, inclusive, and where R is selected from the group consisting of: an unsubstituted aromatic group; an aromatic group substituted by one or more substituents selected from the group consisting of: F, Cl, Br, a lower alkyl group, a lower alkoxy group and a fluorinated lower alkyl group; R'—S(O), where R' is a lower alkyl group, which may be substituted or unsubstituted, branched or straight chain; and $CH_2$=CH, are provided according to the present invention. Methods of synthesis of the present invention include formylation of a starting alkylamine compound having the structural formula: R—$(CH_2)_n$—$NH_2$, where n is an integer in the range of 1-8, inclusive, where R is selected from the group consisting of: an unsubstituted aromatic group; an aromatic group substituted by one or more substituents selected from the group consisting of: F, Cl, Br, a lower alkyl group, a lower alkoxy group and a fluorinated lower alkyl group; R'—S(O), where R' is a lower alkyl group, which may be substituted or unsubstituted, branched or straight chain; and $CH_2$=CH, to produce a formylated intermediate having the structural formula: R—$(CH_2)_n$—NHCHO, where R and n are identical to R and n of the starting alkylamine; and contacting the formylated intermediate with triphosgene and selenium powder in the presence of triethylamine. In a preferred option, the formylated intermediate is contacted with triphosgene and selenium powder in the presence of triethylamine and in the presence of a solvent, such as dichloromethane.

Pharmaceutical compositions are provided according to embodiments of the present invention which include one or more isothiocyanates and/or isoselenocyanates having the structural formula R—$(CH_2)_n$—N=C=X, where n is an integer in the range of 1-8, inclusive, where X is S or Se, and where R is selected from the group consisting of: an aromatic group and a non-aromatic organic group.

Pharmaceutical compositions according to embodiments of the present invention include one or more isothiocyanates and/or isoselenocyanates having the structural formula phenyl-$(CH_2)_n$—N=C=X, where n is an integer in the range of 1-8, inclusive, and where X is S or Se.

Pharmaceutical compositions are provided according to embodiments of the present invention which include an isoselenocyanate having the structural formula selected from the group consisting of:

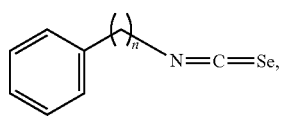

where n is 4 or 6;

and

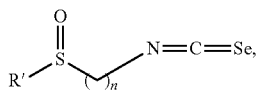

where R' is a substituted or unsubstituted, branched or straight chain, lower alkyl group, and where n is an integer in the range of 3-8, inclusive; and a pharmaceutically acceptable carrier. Optionally, the pharmaceutically acceptable carrier is a particulate carrier. In a further option, the pharmaceutical composition is formulated for topical application.

Methods of treating a subject are provided according to the present invention which include administering an effective amount of a composition including an isoselenocyanate described herein to a subject in need thereof. In embodiments of the present invention, a composition administered to a subject in need thereof includes a phenylalkyl isoselenocyanate having the structural formula:

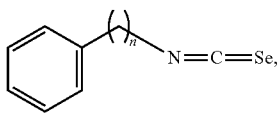

where n is 4 or 6. Optionally, the phenylalkyl moiety is substituted at an available substitutable site. For example, the phenylalkyl may be substituted by one or more substituents selected from the group consisting of: F, Cl, Br, a lower alkyl group, a lower alkoxy group and a fluorinated lower alkyl group.

Embodiments of compositions administered to a subject in need thereof include an isoselenocyanate having the structural formula:

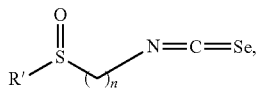

where R' is a substituted or unsubstituted, branched or straight chain, lower alkyl group, and where n is an integer in the range of 3-8, inclusive. Optionally, R' is $CH_3$. In a further option, R' is $CH_3$ and n is 4.

An isoselenocyanate composition is optionally conjugated to glutathione, cysteine or N-acetylcysteine to produce an isoselenocyanate glutathione conjugate; an isoselenocyanate cysteine conjugate; and an isoselenocyanate N-acetylcysteine conjugate for administration to a subject in need thereof.

In embodiments of methods including administration of an isoselenocyanate to a subject, the subject is human.

In further embodiments, the subject has or is at risk of having cancer. In certain embodiments, the subject has cancer or is at risk for cancer characterized by dysregulation of Akt1, Akt2 and/or Akt3. In further embodiments, the cancer is a melanoma.

Methods of treating a subject are provided according to embodiments of the present invention which include administering a therapeutically effective amount of a composition including an isothiocyanate and/or isoselenocyanate to a subject in need thereof, wherein the isothiocyanate or isoselenocyanate has the structural formula: R—$(CH_2)_n$—N=C=X, where n is an integer in the range of 1-8, inclusive, where X is S or Se, and where R is selected from the group consisting of: an aromatic group and a non-aromatic organic group and wherein the subject has a condition characterized by Akt dysregulation, such as cancer, pre-neoplastic hyperproliferation, cancer in-situ, neoplasms, metastasis, tumor or benign growth. In certain embodiments of methods of treatment of a subject, contacting cells characterized by Akt dysregulation with a therapeutic amount of an isothiocyanate and/or isoselenocyanate described herein decreases a component of an Akt signaling pathway selected from the group consisting of: an Akt1 signaling pathway; an Akt2 signaling pathway; an Akt3 signaling pathway; and a combination thereof. For example, contacting the cell with an isothiocyanate and/or isoselenocyanate decreases a component of an Akt signaling pathway selected from pAkt1, pAkt2, pAk3, pPRAS40 and a combination thereof. In embodiments of described methods, treatment of a subject with a therapeutically effective amount of the composition including an isothiocyanate and/or isoselenocyanate is substantially without toxic effect on cells in which Akt is not dysregulated.

Methods of treating a subject are provided according to embodiments of the present invention which include administering a therapeutically effective amount of a composition including an isothiocyanate and/or isoselenocyanate to a subject in need thereof, wherein the isothiocyanate or isoselenocyanate has the structural formula: phenyl-$(CH_2)_n$—N=C=X, where n is an integer in the range of 1-8, inclusive, where X is S or Se, and wherein the subject has a condition characterized by Akt dysregulation, such as cancer, pre-neoplastic hyperproliferation, cancer in-situ, neoplasms, metastasis, tumor or benign growth. Optionally the phenyl group is substituted.

Methods according to embodiments of the present invention include administering a therapeutically effective amount of a composition including an isoselenocyanate and/or an isothiocyanate to a subject wherein the administration detectably increases apoptosis and/or decreases proliferation of cells of the cancer, pre-neoplastic hyperproliferation, cancer in-situ, neoplasms, metastasis, tumor or benign growth.

Optionally, a composition including an isoselenocyanate and/or isothiocyanate according to embodiments of the present invention is formulated for topical application, for instance to treat cancer, pre-neoplastic hyperproliferation, cancer in-situ, neoplasms, metastasis, tumor or benign growth of the skin.

Optionally, methods of the present invention additionally include administration of an adjunct anti-cancer treatment.

A method of modulating Akt dysregulation in a cell is provided according to embodiments of the present invention which includes contacting the cell with an effective amount of an isothiocyanate or isoselenocyanate having the structural formula: R—$(CH_2)_n$—N=C=X, where n is an integer in the range of 1-8, inclusive, where X is S or Se, and where R is selected from the group consisting of: an aromatic group and a non-aromatic organic group. In certain embodiments of methods of modulating Akt dysregulation, contacting the cell with an isoselenocyanate decreases a component of an Akt signaling pathway selected from the group consisting of: an Akt1 signaling pathway; an Akt2 signaling pathway; an Akt3 signaling pathway; and a combination thereof. For example, contacting the cell with an isoselenocyanate decreases a component of an Akt signaling pathway selected from pAkt1, pAkt2, pAk3, pPRAS40 and a combination thereof.

A method of modulating Akt dysregulation in a cell is provided according to embodiments of the present invention which includes contacting the cell with an effective amount of an isothiocyanate or isoselenocyanate having the structural formula: phenyl-$(CH_2)_n$—N=C=X, where n is an integer in the range of 1-8, inclusive, and where X is S or Se. Optionally, the phenyl group is substituted.

A method of modulating Akt dysregulation in a cell is provided according to embodiments of the present invention which includes contacting the cell with an effective amount of an isoselenocyanate having the structural formula: R—$(CH_2)_n$—N=C=Se, where n is an integer in the range of 1-8, inclusive, and where R is selected from the group consisting of: an aromatic group and a non-aromatic organic group. In certain embodiments of methods of modulating Akt dysregulation, contacting the cell with an isoselenocyanate decreases a component of an Akt signaling pathway selected from the group consisting of: an Akt1 signaling pathway; an Akt2 signaling pathway; an Akt3 signaling pathway; and a combination thereof. For example, contacting the cell with an isoselenocyanate decreases a component of an Akt signaling pathway selected from pAkt1, pAkt2, pAk3, pPRAS40 and a combination thereof.

BRIEF DESCRIPTION OF THE DRAWINGS

FIG. 19 is a bar graph showing the effects of topically applied PBITC or ISC-4 on reconstructed human skin containing GFP tagged UACC 903 human melanoma cells;

FIG. 20 is a pair of line graphs showing the effect of topical ISC-4 application on melanoma tumor growth in vivo.

DETAILED DESCRIPTION OF THE INVENTION

Figure 1A:
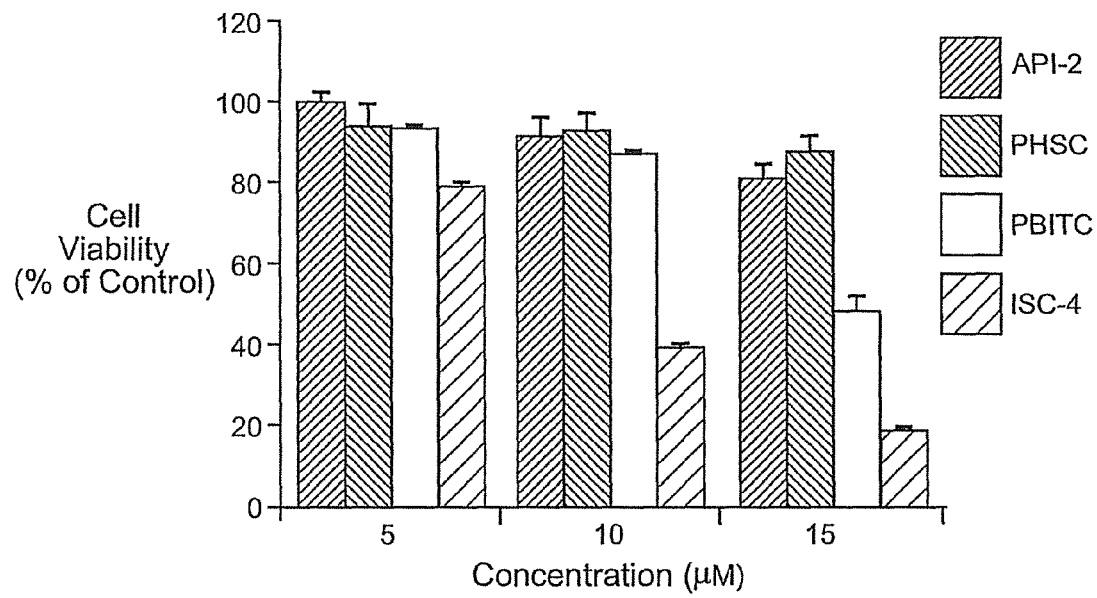
FIG. 1A is a bar graph showing a comparison of cell viability following exposure to PBITC or ISC-4, compared to controls.

Anti-cancer compositions and methods are provided according to embodiments of the present invention. In certain embodiments, the present invention relates to compositions including one or more isothiocyanates and/or isoselenocyanates, methods for treatment and/or prevention of pathological conditions in a subject using one or more isothiocyanates and/or isoselenocyanates and methods for synthesis of particular isoselenocyanates.

A composition provided according to embodiments of the present invention includes one or more compounds having the structural formula: R—$(CH_2)_n$—N=C=Se, where n is an integer in the range of 1-8, inclusive, where R is an aromatic group or a non-aromatic organic group.

The term "aromatic" as used herein refers to an optionally substituted monocyclic or bicyclic hydrocarbon ring system containing at least one unsaturated aromatic ring. Non-limiting examples of aromatic groups include phenyl and napthyl.

In particular embodiments, compositions of the present invention are phenylalkyl isoselenocyanates having the structural formula:

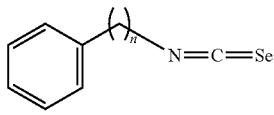

where n is 1-8.

R is optionally an aromatic group substituted by one or more of the following: F, Cl, Br, a lower alkyl group, a lower alkoxy group or fluorinated lower alkyl group, such as $CF_3$. In particular embodiments, R is phenyl group substituted by one or more of the following: F, Cl, Br, a lower alkyl group, a lower alkoxy group or fluorinated lower alkyl group, such as $CF_3$.

The term "lower alkoxy" as used herein refers to a straight chain or branched hydrocarbon group containing from 1-4 carbon atoms which is appended to the parent molecular moiety through an oxygen atom. Illustrative examples of lower alkyl groups are methoxy, ethoxy, propoxy, 2-propoxy, butoxy and tert-butoxy.

The term "lower alkyl" as used herein refers to a straight chain or branched hydrocarbon group containing from 1-4 carbon atoms. Illustrative examples of lower alkyl groups are methyl, ethyl, iso-propyl, n-propyl, n-butyl, iso-butyl, sec-butyl and tert-butyl.

In particular embodiments, a composition of the present invention includes a sulfoxide composition according to the present invention having the structural formula:

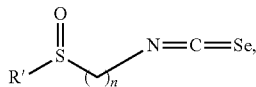

where R' is a lower alkyl group, which may be substituted or unsubstituted, branched or straight chain, and where n is an integer in the range of 1-8, inclusive.

In certain embodiments, a composition of the present invention includes a sulfoxide composition according to the present invention having the structural formula:

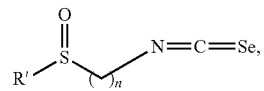

where R' is a lower alkyl group, which may be substituted or unsubstituted, branched or straight chain, and where n is an integer in the range of 3-8, inclusive.

In still further embodiments, a composition of the present invention includes a sulfoxide composition according to the present invention having the structural formula:

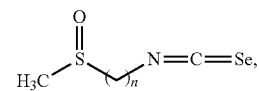

where $CH_3$ can be substituted or unsubstituted and where n is an integer in the range of 3-8, inclusive.

Embodiments of a composition according to the present invention have the structural formulas: $CH_3$—S(O)—$(CH_2)_3$—N=C=Se (termed ISC-SFN3); $CH_3$—S(O)—$(CH_2)_4$—N=C=Se (termed ISC-SFN4 and SFN Iso Se); $CH_3$—S(O)—$(CH_2)_5$—N=C=Se (termed ISC-SFN5); $CH_3$—S(O)—$(CH_2)_6$—N=C=Se (termed ISC-SFN6); $CH_3$—S(O)—$(CH_2)_7$—N=C=Se (termed ISC-SFN7) and $CH_3$—S(O)—$(CH_2)_8$—N=C=Se (termed ISC-SFN8) Optionally, $CH_3$ is substituted or unsubstituted.

In certain embodiments, R in the structural formula: R—$(CH_2)_n$—N=C=Se, where n is an integer in the range of 1-8, is a substituted aromatic group. In further embodiments, R is a phenyl group substituted at one or more substitutable sites by Cl, Br, F, methyl, methoxy, and/or a fluorinated lower alkyl group, such as $CF_3$.

The non-aromatic organic group optionally includes one or more heteroatoms such as S, N, O and/or P.

In further embodiments where R is a non-aromatic organic group, R is $CH_2$=CH. For example, where R is $CH_2$=CH, an isoselenocyanate has the formula: $CH_2$=CH—$CH_2$—N=C=Se.

In a further option, the group $(CH_2)_n$ in the formula R—$(CH_2)_n$—N=C=Se, is substituted. For example, the group $(CH_2)$, in the formula R—$(CH_2)_n$—N=C=Se, is substituted by one or more of the following: F, Cl, Br, a lower alkyl group, a lower alkoxy group or fluorinated lower alkyl group, such as $CF_3$.

Compositions including mixtures of two or more isoselenocyanates are also specifically contemplated and are considered to be within the scope of the present invention.

Structures of particular compounds described herein, along with abbreviations used, are shown below. Particular naturally occurring and synthetic phenylalkyl isothiocyanate compounds with increasing chain length in the left column; phenylalkyl isoselenocyanates of the present invention are shown in the center column; and phenylhexyl selenocyanate in the right column. Phenylhexyl selenocyanate (PHSC) is used as a control compound in particular tests described herein since it is similar to ISC-6 in structure and contains selenium.

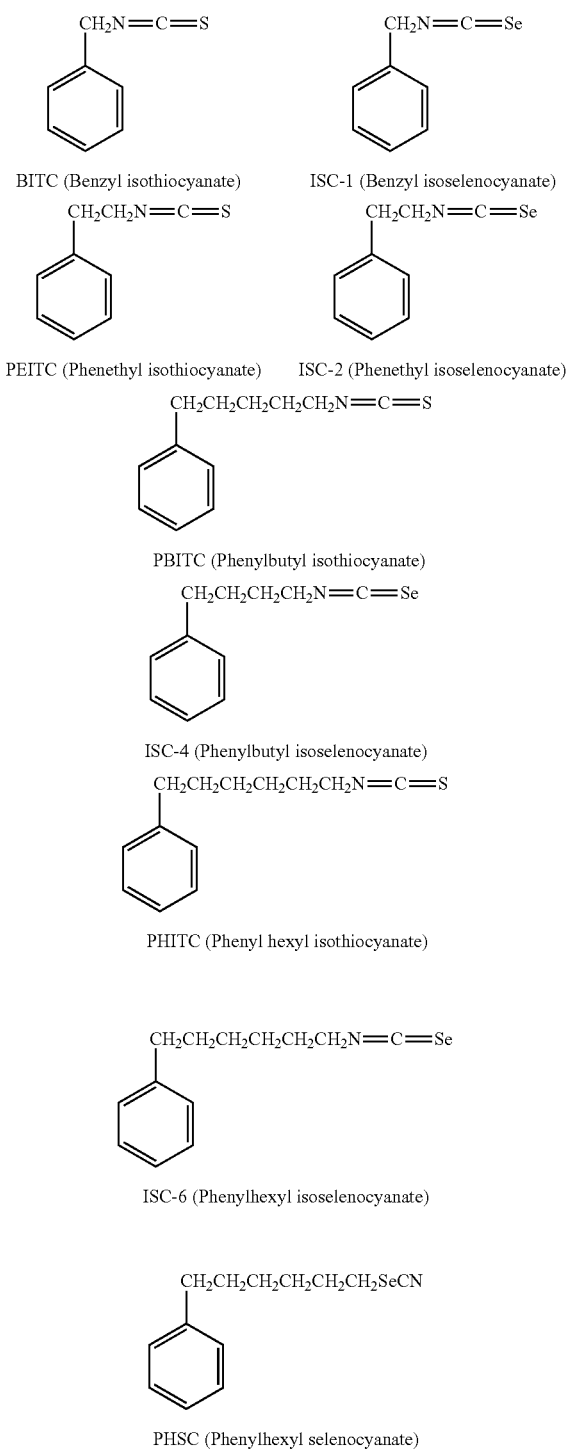

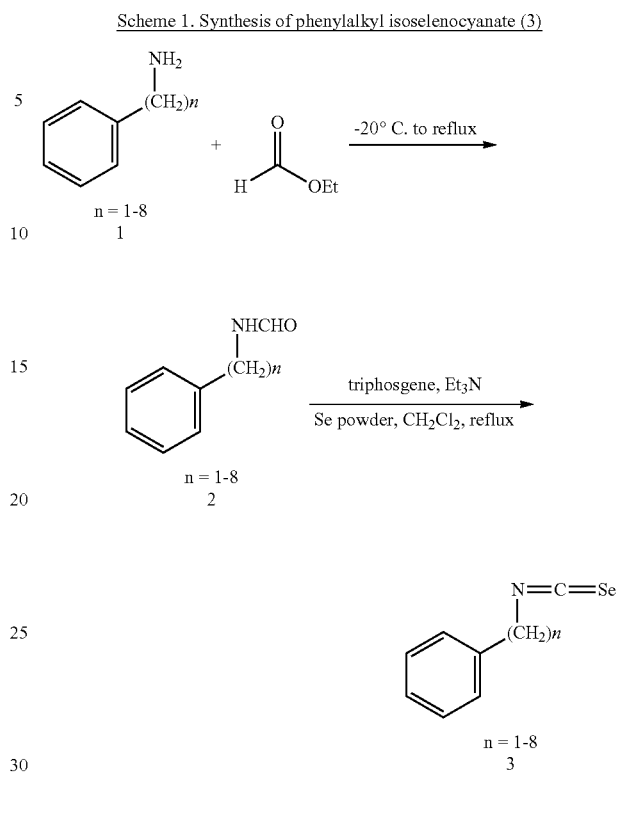

Scheme 1. Synthesis of phenylalkyl isoselenocyanate (3)

Methods for synthesis of isothiocyanates and isoselenocyantes derivatives with a substituted phenyl ring are also provided by the present invention.

Substituted phenyl ring analogs of phenylalkyl isoselenocyanates are synthesized (Scheme 2a), following substantially identical methodologies as described in Scheme 1 for the synthesis of isoselenocyanates. In a similar manner, substituted phenylalkyl isothiocyanates are synthesized by treating the corresponding substituted arylalkylamine with thiophosgene and sodium hydroxide as shown in Scheme 2b. Several combinations of substitutions of phenyl ring (e.g. 2-, 3- or 4-chloro (Cl), bromo (Br), fluoro (—F), methyl ($CH_3$), methoxy ($OCH_3$) and trifluoromethyl (—$CF_3$) substituted arylalkyl isothiocyanates and isoselenocyanates are synthesized starting from corresponding appropriately substituted 2-, 3-, and 4-Cl/Br/F/$CH_3$/$OCH_3$/$CF_3$-phenylalkylamines.

Methods for synthesis of an isoselenocyanate are provided according to embodiments of the present invention.

A process for synthesis of a compound according to embodiments of the present invention is shown in Scheme 1. Treatment of a phenylalkylamine (1) with ethyl formate leads to the formation of intermediate 2, which on reaction with selenium powder in the presence of triphosgene and triethylamine, in refluxing dichloromethane, furnishes the desired isoselenocyanate (3).

Scheme 2a. Synthesis of substituted phenylalkyl isoselenocyanate

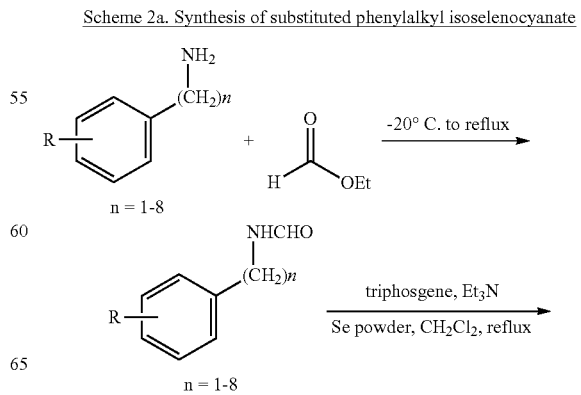

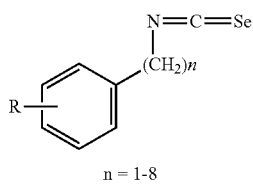

n = 1-8

R = Cl, Br, F, CH₃, OCH₃, CF₃

Scheme 2b. Synthesis of substituted isothiocyanate

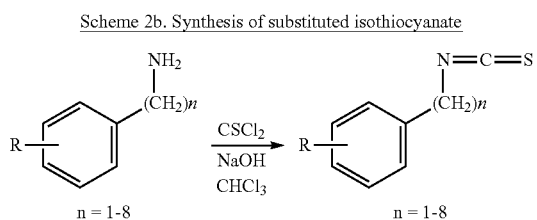

n = 1-8

R = Cl, Br, F, CH₃, OCH₃, CF₃

Methods of synthesis of isosteric selenium analogs of non-aromatic naturally occurring isothiocyanates are provided by the present invention. For example, methods of synthesis of isosteric selenium analogs of sulforaphane i.e., 1-isoselenocyanato-4-(methylsulfinyl)butane (ISC-SFN4, also called SFN Iso Se herein), are provided according to embodiments of the present invention. The synthetic route followed is outlined in Scheme 3. The key intermediate 1-amino-4-(methylsulfinyl)butane (1 in scheme 3) is synthesized and subjected to a sequence of reactions as shown in Scheme 3 to obtain the desired ISC-SFN4 (3). Further analogs, including ISC-SFN3, ISC-SFN6, ISC-SFN7, and ISC-SFN8 which are isosteric selenium analogs of corresponding naturally occurring sulfoxide isothiocyanate analogs with varying alkyl chain length are synthesized using a similar synthetic strategy.

Scheme 3. Synthesis of ISC-SFN3, ISC-SFN4, ISC-SFN5, ISC-SFN6, ISC-SFN7, and ISC-SFN8

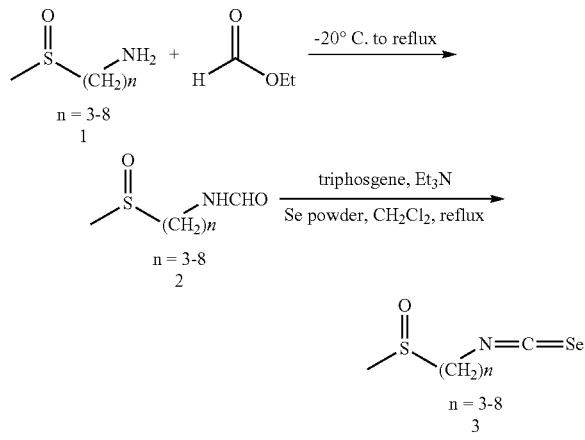

In further embodiments, an allyl isoselenocyanate is synthesized according to embodiments of the present invention starting from allylamine as detailed in Scheme 4.

Scheme 4. Synthesis of allyl isoselenocyanate

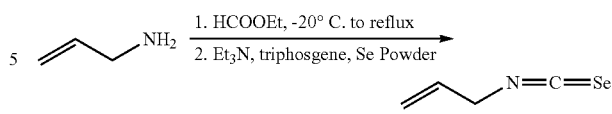

Conjugate Compositions

A compound of the present invention is conjugated to one or more property-enhancing moieties according to embodiments of the present invention for modification of one or more characteristics of the compound. The present invention provides conjugates of organic isothiocyanates and/or isoselenocyanates, in order to reduce toxicity, increase solubility and/or increase bioavailability in particular embodiments of the present invention. Methods of synthesis of such conjugates are also provided by embodiments of the presently described invention.

For example, in particular embodiments, a compound of the present invention is conjugated to a water solubility-enhancing moiety, to yield a conjugate which is more water soluble than the compound. Thus, in particular embodiments, water soluble isothiocyanate or isoselenocyanate compounds of the present invention are conjugated to glutathione (GSH), cysteine (Cys) or N-acetylcysteine (NAC) to yield the corresponding GSH-, Cys-, or NAC-conjugate.

An exemplary structure of a glutathione conjugate of a phenylalkyl isoselenocyanate, where n is an integer in the range of 1-8, inclusive:

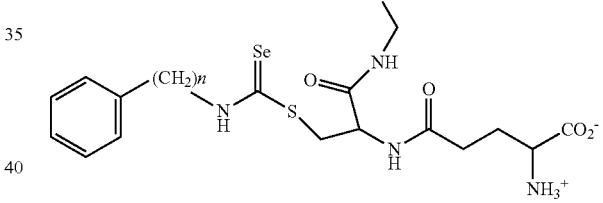

An exemplary structure of a cysteine conjugate of a phenylalkyl isoselenocyanate, where n is an integer in the range of 1-8, inclusive:

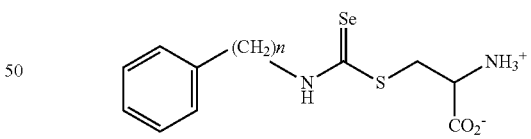

An exemplary structure of an N-acetylcysteine conjugate of a phenylalkyl isoselenocyanate, where n is an integer in the range of 1-8, inclusive:

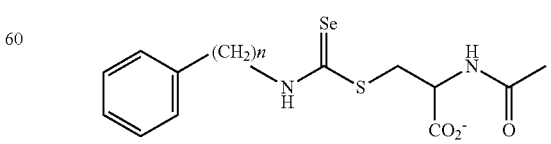

The NAC-conjugates of organic isoselenocyanates, such as ISC-4 and ISC-6, are made by reacting corresponding isoselenocyanate with NV acetylcysteine in aqueous ethanol (50%) at room temperature under nitrogen atmosphere. The GSH or cysteine conjugates of isoselenocyanates are synthesized following a similar procedure.

Compositions according to embodiments of the present invention prevent and inhibit cancer cell multiplication and tumor development and are considered useful as chemotherapeutic and chemopreventive agents. In addition, isoselenocyanate compositions according to embodiments of the present invention induce cell death in cancer cells more effectively than corresponding isothiocyanates or derivatives thereof. Further, animal studies show significant reduction in melanoma tumor development by isoselenocyanates of the present invention at doses three times lower than those of corresponding isothiocyanates, without significant toxicity.

Methods and compositions are provided according to the present invention for treating cancer. Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer.

A therapeutically effective amount of a composition is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an isoselenocyanate composition, a therapeutically effective amount of a composition is effective to ameliorate or prevent one or more signs and/or symptoms of the condition. For example, a therapeutically effective amount of a composition is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an isoselenocyanate composition.

In particular embodiments, cancers treated using methods and compositions described herein are characterized by Akt dysregulation.

Akt, a serine/threonine protein kinase also known as protein kinase B, has a stimulatory effect on cell cycle progression, cell proliferation and inhibition of apoptosis. Akt proteins, nucleic acids and signaling pathway components are described, for instance, see Testa, J. R. et al., PNAS, 98:10983-10985; Fayard, E. et al., J. Cell Sci., 118:5675-5678, 2005; Cheng, J. and S, Nicosia, (2001) AKT signal transduction pathway in oncogenesis, in Encyclopedic Reference of Cancer, D. Schwab, Editor. 2001, Springer: Berlin, Germany, p. 35-7; Datta, S. R., et al. (1999) Cellular survival: a play in three Akts. Genes Dev, 13(22): 2905-27; Fayard, E. et al. (2005) J Cell Sci, 118 (Pt 24: 5675-8; Mirza, A. M., Fayard, E. et al. (2000) 2000. 11 (6: 279-92; Nicholson, K. M. and N. G. Anderson, (2002) Cell Signal, 2002, 14(5): p. 381-95; Paez, J. and W. Sellers, (2003) P13K/PTEN/Akt Pathway: A Critical Mediator of Oncogenic Signaling, in Signal Transduction in Cancer, D. Frank, Editor. 2003, Kluwer Academic Publishers: Netherlands; and Testa, J. R.; P. N. Tsichlis, (2005) Oncogene, 24(50): 7391-3 and other references listed herein.

Akt family members, Akt1, Akt2 and Akt3, are activated by phosphorylation, membrane translocation, increases in gene copy number and/or loss of a negative regulatory phosphatase, PTEN. Increased activation of Akt, including increased levels of Akt and/or increased levels of phosphorylated Akt is an indicator of Akt dysregulation associated with proliferation and cell survival in pathogenic conditions, such as cancer.

Akt3 is active in ~70% of melanomas. While all three Akt isoforms are expressed in melanocytes and melanoma cells, Akt3 is the predominantly active family member. Dysregulated Akt3 activity in melanoma cells reduces cellular apoptosis mediated through caspase-3, thereby promoting melanoma tumor development.

Akt dysregulation is determined, for instance, by measurement of Akt gene copy number, Akt protein or RNA levels and/or levels of phosphorylated Akt, in cells known or suspected to be dysplasic, pre-cancerous, cancerous, metastatic or otherwise characterized by abnormal cell proliferation compared to normal cells. Assays for Akt dysregulation include, but are not limited to immunoassays and nucleic acid assays.

Methods of treating a subject are provided according to embodiments of the present invention which include administering a therapeutically effective amount of a composition including an isothiocyanate and/or isoselenocyanate to a subject in need thereof, wherein the isothiocyanate or isoselenocyanate has the structural formula: R—$(CH_2)_n$—N=C=X, where n is an integer in the range of 1-8, inclusive, where X is S or Se, and where R is selected from the group consisting of: an aromatic group and a non-aromatic organic group and wherein the subject has a condition characterized by Akt dysregulation, such as cancer, pre-neoplastic hyperproliferation, cancer in-situ, neoplasms, metastasis, tumor or benign growth. In certain embodiments of methods of treatment of a subject, contacting cells characterized by Akt dysregulation with a therapeutic amount of an isothiocyanate and/or isoselenocyanate described herein decreases a component of an Akt signaling pathway selected from the group consisting of: an Akt1 signaling pathway; an Akt2 signaling pathway; an Akt3 signaling pathway; and a combination thereof. For example, contacting the cell with an isothiocyanate and/or isoselenocyanate decreases a component of an Akt signaling pathway selected from pAkt1, pAkt2, pAk3, pPRAS40 and a combination thereof. In embodiments of described methods, treatment of a subject with a therapeutically effective amount of the composition including an isothiocyanate and/or isoselenocyanate is substantially without toxic effect on cells in which Akt is not dysregulated.

Methods of treating a subject are provided according to embodiments of the present invention which include administering a therapeutically effective amount of a composition including an isothiocyanate and/or isoselenocyanate to a subject in need thereof, wherein the isothiocyanate or isoselenocyanate has the structural formula: phenyl-$(CH_2)_n$—N=C=X, where n is an integer in the range of 1-8, inclusive, where X is S or Se, and wherein the subject has a condition characterized by Akt dysregulation, such as cancer, pre-neoplastic hyperproliferation, cancer in-situ, neoplasms, metastasis, tumor or benign growth.

Methods of treating a subject are provided according to embodiments of the present invention which include administering a therapeutically effective amount of a composition including an isothiocyanate and/or isoselenocyanate to a subject in need thereof, wherein the isothiocyanate or isoselenocyanate is BITC, PEITC, PBITC, PHITC, ISC-1, ISC-2, ISC-4 or ISC-6 and wherein the subject has a condition characterized by Akt dysregulation, such as cancer, pre-neoplastic hyperproliferation, cancer in-situ, neoplasms, metastasis, tumor or benign growth.

Methods of treating a subject are provided according to embodiments of the present invention which include administering an effective amount of a composition including an isoselenocyanate to a subject in need thereof.

A method of treating a subject is provided according to embodiments of the present invention which includes administering to a subject in need thereof a therapeutically effective amount of a an isoselenocyanate compound having the structural formula: R—$(CH_2)_n$—N=C=Se, where n is an integer in the range of 1-8, inclusive, where R is an aromatic group or a non-aromatic organic group.

In embodiments of the present invention, a method of treating a subject includes administering an effective amount of an isoselenocyanate having the structural formula:

$$R'\overset{O}{\underset{\|}{S}}(\phantom{x})_n N=C=Se,$$

where R' is a substituted or unsubstituted, branched or straight chain, lower alkyl group, and where n is an integer in the range of 3-8, inclusive.

In embodiments of the present invention, a method of treating a subject includes administering an effective amount of an isoselenocyanate having the structural formula:

$$R'\overset{O}{\underset{\|}{S}}(\phantom{x})_n N=C=Se,$$

where R' is $CH_3$ and where n is an integer in the range of 1-8, inclusive.

In embodiments of the present invention, a method of treating a subject includes administering an effective amount of an isoselenocyanate having the structural formula:

$$R'\overset{O}{\underset{\|}{S}}(\phantom{x})_n N=C=Se,$$

where R' is $CH_3$ and n is 4.

In embodiments of the present invention, a method of treating a subject, includes administering an effective amount of a phenylalkyl isoselenocyanate having the structural formula:

$$\text{Ph}(\phantom{x})_n N=C=Se,$$

where n is 4 or 6.

Optionally, an administered isoselenocyanate is an isoselenocyanate glutathione conjugate; an isoselenocyanate cysteine conjugate; or an isoselenocyanate N-acetylcysteine conjugate.

Optionally, an administered isoselenocyanate is a pharmaceutically acceptable salt, ester or amide of an isoselenocyanate described herein.

Isothiocyanate and/or isoselenocyanate compositions are provided according to embodiments of the present invention which inhibit tumor growth by inhibiting an Akt signaling cascade, particularly an Akt3 signaling cascade, in cells characterized by Akt dysregulation in certain embodiments.

Methods including administration of one or more isothiocyanates and/or isoselenocyanates to a subject in need thereof are provided according to particular embodiments of the present invention which have utility, for example, in inhibiting the Akt signaling cascade and inhibiting cancer cells.

Inhibitors of the Akt signaling cascade according to embodiments of the present invention have utility in treatment of subject having cancer or at risk of having cancer in which Akt deregulation occurs, such as in melanoma and other cancers including, but not limited to, cancers of the prostate, breast, brain, ovary, lung, colon, connective tissues (sarcomas) and soft tissue.

Methods of modulating an Akt protein, such as an Akt1, Akt2 and/or an Akt3 protein, in a cell are provided according to embodiments of the present invention which include contacting the cell with an effective amount of an isoselenocyanate.

Pharmaceutical compositions including an isoselenocyanate of the present invention are also provided according to embodiments of the present invention.

A pharmaceutical composition includes an isoselenocyanate of the present invention and a pharmaceutically acceptable carrier in particular embodiments of the present invention. The term "pharmaceutically acceptable carrier" refers to a carrier which is substantially non-toxic to a subject to which the composition is administered and which is substantially chemically inert with respect to a selenium-containing compound of the present invention.

A pharmaceutical composition according to the invention generally includes about 0.1-99% of an isoselenocyanate of the present invention. Combinations of isoselenocyanates in a pharmaceutical composition are also considered within the scope of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, fluorocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, pipsulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, selenium-containing compound of the present invention is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular embodiments, compositions of the present invention are formulated for topical application. In further particular embodiments, compositions of the present invention are formulated for topical application and are characterized by less than 10% absorption of an active ingredient in the composition into the system of an individual treated topically. In still further particular embodiments, compositions of the present invention are formulated for topical application and are characterized by less than 9%, 8%, 7%, 6%, 5%, 4%, 3%, 2%, 1% absorbtion of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular embodiments. Topical dosage forms such as ointment, lotion, cream or gel bases are described in Remington: The Science and Practice of Pharmacy, 21$^{st}$ Ed., Lippincott Williams & Wilkins, 2006, p. 880-882 and p. 886-888; and in Allen, L. V. et al., Ansel's Pharmaceutical Dosage Forms and Drug Delivery Systems, 8$^{th}$ Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, 21$^{st}$ Ed., Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

The term subject refers to an individual in need of treatment for a pathological condition, particularly cancer, and generally includes mammals and birds, such as, but not limited to, humans, other primates, cats, dogs, cows, horses, rodents, pigs, sheep, goats and poultry.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of cancer.

With regard to administration of isoselenocyanates to a mammalian subject, particular exemplary effective dosage ranges without significant systemic toxicity are described in terms of amounts of selenium administered via administration of the isoselenocyanate. Thus, for example, when delivered by a parenteral route, such as intraperitoneal or intravenous, an exemplary therapeutically effective dosage of an isoselenocyanate is in the range of about 1-4 ppm selenium, administered three times per week. It is noted that the dose range "about 1-4 ppm selenium" refers to a dose of "about 1 mg/kg-4 mg/kg of selenium." For example, a dose of 3 ppm selenium when referring to ISC-4 is equivalent to a dose of 9.1 mg/kg of ISC-4. Similarly, a dose of 3 ppm selenium when referring to ISC-6 is equivalent to a dose of 10.17 mg/kg of ISC-6. In a further example, when delivered topically, an exemplary therapeutically effective dosage of ISC-4 or ISC-6 is in the range of about 0.1-1 ppm selenium, administered daily. In a further example, when delivered orally, an exemplary therapeutically effective dosage of an isoselenocyanate is in the range of about 1-15 ppm selenium.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Advantageously, anti-cancer compounds according to embodiments of the present invention are formulated to achieve lipid-solubility and/or aqueous-solubility.

In particular embodiments, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular embodiments, a particulate carrier is formulated such that particles have an average particle size in the range of about 1 nm-100 nm.

Embodiments of inventive compositions and methods are illustrated in the following examples. These examples are provided for illustrative purposes and are not considered limitations on the scope of inventive compositions and methods.

EXAMPLES

Example 1

Cell Lines and Culture Conditions

The human metastatic melanoma cell lines UACC 903 and 1205 Lu; normal human fibroblast cells (FF2441) are maintained in DMEM (Invitrogen, Carlsbad, Calif.) supplemented with 10% FBS (Hyclone, Logan, Utah). Vertical growth phase (VGP) melanoma cell line WM115 is maintained in Tu2% medium lacking calcium chloride, supplemented with 2% heat treated (56° C. for 30 minutes) FBS and L-glutamine (Mediatech, Handon, Va.) as described in Stahl J M, et al., Cancer Res 2004; 64:7002-10.

Colon adenocarcinoma cell line (Cato-2, ATCC No. HTB-37) is grown either in Advanced DMEM supplemented with 10% heat treated (56° C. for 30 minutes) FBS and L-glutamine. Fibrosarcoma (HT-1080; ATCC No. CCL-121), prostate adenocarcinoma (PC-3; ATCC No. CRL-1435), breast adenocarcinoma cell line (MDA-MB-231; ATCC No. HTB-26), glioblastoma cell line (T98G; ATCC No. CRL-1690) and human melanoma cell line UACC903 are grown in DMEM supplemented with 10% FBS.

Example 2

Chemical Synthesis

Synthetic methods described in Examples 2-12 refer generally to the following numbered structures:

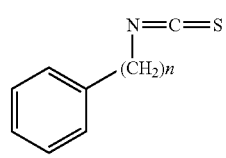

1

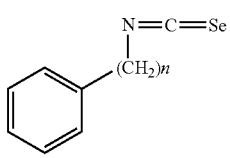

2

Melting points were recorded on a Fisher-Johns melting point apparatus and are uncorrected. Unless stated otherwise, proton NMR spectra were recorded in a Bruker AM 360WB instrument using $CDCl_3$ as solvent. The chemical shifts are reported in ppm downfield from TMS. High-resolution MS (EI) are determined at the Chemistry Instrumentation Center, State University of New York at Buffalo, N.Y. Thin-layer chromatography (TLC) is developed on aluminum-supported, pre-coated silica gel plates (EM Industries, Gibbstown, N.J.). Column chromatography was conducted on silica gel (60-200 mesh). Benzyl isothiocyanate (BITC, 1a), phenylethyl isothiocyanate (PEITC, 1b), and phenylbutylisothiocyanate (PBITC, 1c) are obtained from commercial sources. Phenylhexylisothiocyanate (PHITC, 1d) is synthesized as described in Morse, M. A. et al., Cancer Res 1991, 51, (7), 1846-50.

Example 3

A general method for the synthesis of phenylalkylformamides is described in Elliott, M. C.; Williams, E., Synthesis and reactions of partially reduced biisoquinolines. Org Biomol Chem 2003, 1, (17), 3038-47. Ethyl formate (120 mmol) was added dropwise to phenylalkylamine (40 mmol) at room temperature and the resulting mixture was refluxed for 4-6 h. The excess ethyl formate was removed under reduced pressure to yield the corresponding phenylakylformamide as an oil.

Phenylethylformamide: (AS3.090) $^1$H NMR ($CDCl_3$) δ 2.84 (t, 2H, J=6.9 Hz), 3.57 (dt, 2H, J=6.9 Hz and 6.6 Hz), 5.68 (br d, 1H, NH), 7.15-7.35 (m, 5H), 8.12 (s, 1H, CHO); HRMS (EI) calcd for $C_9H_{11}NO$, 149.0835. found, 149.0839.

Phenylbutylformamide. $^1$H NMR ($CDCl_3$) δ 1.56-1.62 (m, 2H), 1.66-1.72 (m, 2H), 2.66 (t, 2H, J=6.5 Hz), 3.35 (dt, 2H, J=7.0 and 6.5 Hz), 5.92 (br s, 1H), 7.18-7.24 (m, 2H), 7.29-7.33 (m, 2H), 8.19 (s, 1H); HRMS (EI) calcd for $C_{11}H_{15}NO$, 177.1148. found, 177.1149.

Phenylhexylformamide. $^1$H NMR ($CDCl_3$) δ 1.36-1.41 (m, 4H), 1.52-1.58 (m, 2H), 1.61-1.67 (m, 2H), 2.63 (t, 2H, J=7.5 Hz), 3.30 (dt, 2H, J=7.0 and 6.5 Hz), 5.58 (br s, 1H), 7.18-7.21 (m, 3H), 7.28-7.31 (m, 2H), 8.19 (s, 1H); HRMS (EI) calcd for $C_{13}H_{19}NO$, 205.1461. found, 205.1462.

Example 4

Isoselenocyanates are synthesized using a modified method described in Fernández-Bolaños, J. G., López, O., Ulgar, V., Maya, I., and Fuentes, J., Synthesis of O-unprotected glycosyl selenoureas. A new access to bicyclic sugar isoureas. Tetrahedron Lett. 2004, 45, 4081-4084. Solid triphosgene is used in a one-pot dehydration of the formamides in refluxing dichloromethane (Scheme 5).

Scheme 5

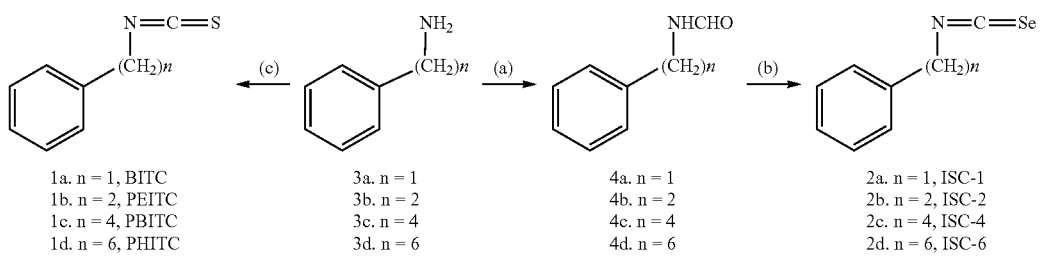

| 1a. n = 1, BITC | 3a. n = 1 | 4a. n = 1 | 2a. n = 1, ISC-1 |
| 1b. n = 2, PEITC | 3b. n = 2 | 4b. n = 2 | 2b. n = 2, ISC-2 |
| 1c. n = 4, PBITC | 3c. n = 4 | 4c. n = 4 | 2c. n = 4, ISC-4 |
| 1d. n = 6, PHITC | 3d. n = 6 | 4d. n = 6 | 2d. n = 6, ISC-6 |

Scheme 5 shows synthesis of compounds 1 and 2; Reagents and conditions: (a) $C_2H_5OCHO$, −20° C. to reflux (b) $Et_3N$, triphosgene, Se powder, $CH_2Cl_2$, reflux (c) $CSCl_2$, NaOH.

General Experimental Procedure for the Synthesis of ISC Compounds

The synthetic strategy involves the formylation of phenylalkylamines, followed by treatment with triphosgene and selenium powder in the presence of triethylamine to furnish the desired phenylalkyl isoselenocyanates (2) in good yields as oils.

The compounds are purified by silica gel column chromatography and are characterized on the basis of NMR and high-resolution MS data. (Pure isolated compounds are light yellow (ISC-1 and ISC-2) to colorless (ISC-4 and ISC-6) which tend to get a little darker after storing for longer time).

In a particular example, to a refluxing mixture of the aryl alkyl formamides (1.5 mmol), triethylamine (6.4 mmol) in $CH_2Cl_2$ (5 mL) and 4 Å molecular sieves was added dropwise a solution of triphosgene (0.8 mmol) in $CH_2Cl_2$ (2 mL) for a period of 1 hour. After the addition was complete, the mixture was refluxed for an additional 2.5 hour. Selenium powder (3.0 mmol) was then added and the resulting mixture was refluxed for other 6-8 hours. The mixture is cooled, filtered, and the solvent was evaporated to yield the crude mixture, which is purified by silica gel column chromatography to afford isoselenocyanates.

In a further example, a solution of triphosgene (5.0 mmol) in $CH_2Cl_2$ (15 mL) is added over a 1 hour period to a refluxing mixture of phenylalkylformamides (10.0 mmol), triethylamine (43.0 mmol) and 4 Å molecular sieves in $CH_2Cl_2$ (35 mL). The mixture is then refluxed for an additional 2.5 hours. Selenium powder (20 mmol) is then added and resulting mixture refluxed for 6-8 hours. Mixture is cooled, filtered, and solvent evaporated yielding a crude mixture, which is purified by silica gel column chromatography generating pure isoselenocyanates. Isothiocyanates and isoselenocyanates are >99% pure.

Phenylalkyl isothiocyanates are obtained commercially (BITC, PEITC, and PBITC). PHITC is synthesized as described in Morse, M. A. et al., Cancer Res 1991, 51, (7), 1846-50. Phenylhexylamine (3d) required for the synthesis of 1d is synthesized by converting phenylhexyl chloride to the corresponding azide by treatment with sodium azide in DMF, followed by generation of the 3d by reduction of azide with lithium aluminium hydride as described in Gopalakrishnan, G. et al., J. Labelled. Comp. Radiopharma. 1988, 25, (4), 383-393.

Example 5

Benzyl Isoselenocyanate (2a)

To a refluxing mixture of the formamides (1.5 mmol), triethylamine (6.4 mmol) in $CH_2Cl_2$ (5 mL) and 4 Å molecular sieves was added dropwise a solution of triphosgene (0.8 mmol) in $CH_2Cl_2$ (2 mL) for a period of 1 h. After the addition was complete, the mixture was refluxed for an additional 2.5 h. Selenium powder (3.0 mmol) was then added and the resulting mixture was refluxed for other 6 h. The mixture was cooled, filtered, and the solvent was evaporated to yield the crude mixture, which was purified by silica gel column chromatography to afford isoselenocyanates. (AS3.094): viscous oil, $^1$H NMR (CDCl$_3$) δ 4.81 (s, 2H, CH$_2$), 7.30-7.44 (m, 5H); HRMS (EI) calcd for $C_8H_7NSe$, 196.9738. found, 196.9741.

Example 6

Phenylethyl Isoselenocyanate (2b)

(AS3.091) A mixture of phenylethylformamide (g, 1.5 mmol), triethylamine (6.4 mmol), 4 Å molecular sieves (g), triphosgene (0.8 mmol), and selenium powder (3.0 mmol) in $CH_2Cl_2$ was refluxed and worked up as mentioned for 2a. The crude residue thus obtained was purified by silica gel column chromatography (EtOAc/hexanes 2:98) to give 0.96 g (95%) of 2b as an oil. $^1$H NMR (CDCl$_3$) δ 3.03 (t, 2H, J=6.9 Hz), 3.81 (t, 2H, J=6.9 Hz) 7.20-7.38 (m, 5H); HRMS (EI) calcd for $C_9H_9NSe$, 210.9895. found, 210.9892.

Example 7

Phenylbutyl Isoselenocyanate (2c)

A mixture of phenylbutyl formamide (g, 1.5 mmol), triethylamine (6.4 mmol), 4 Å molecular sieves (g), triphosgene (0.8 mmol), and selenium powder (3.0 mmol) in $CH_2Cl_2$ was refluxed and worked up as mentioned for 2a. The crude residue thus obtained was purified by silica gel column chromatography (EtOAc/hexanes 2:98) to give 0.96 g (95%) of 2c as an oil. $^1$H NMR (CDCl$_3$) δ 1.74-1.76 (m, 4H), 2.66 (t, 2H, J=6.6 Hz), 3.60 (t, 2H, J=5.6 Hz), 7.15-7.32 (m, 5H); HRMS (EI) calcd for $C_{11}H_{13}NSe$, 239.0208. found, 239.0211.

Example 8

Phenylhexyl Isoselenocyanate (2d)

A mixture of phenylbutyl formamide (g, 1.5 mmol), triethylamine (6.4 mmol), 4 Å molecular sieves (g), triphosgene (0.8 mmol), and selenium powder (3.0 mmol) in $CH_2Cl_2$ was refluxed and worked up as mentioned for 2a. The crude residue thus obtained was purified by silica gel column chromatography (EtOAc/hexanes 2:98) to give 0.96 g (95%) of 2d as an oil. $^1$H NMR (CDCl$_3$) δ 1.37-1.43 (m, 2H), 1.45-1.51 (m, 2H), 1.67 (dt, 2H, J=15.2 and 7.6 Hz), 1.75 (dt, 2H, J=14.9 and 6.7 Hz), 2.64 (t, 2H, J=7.6 Hz), 3.60 (t, 21-1, J=6.7 Hz), 7.19-7.25 (m, 3H), 7.32-7.40 (m, 2H); HRMS (EI) calcd for $C_{13}H_{17}NSe$, 267.0521. found, 267.0529.

Example 9

ISC-4-NAC Conjugate (5)

Scheme 6 shows the synthesis of NAC conjugate (5) of ISC-4. The IC$_{50}$ of 5 (UACC 903M cells)=17±2.

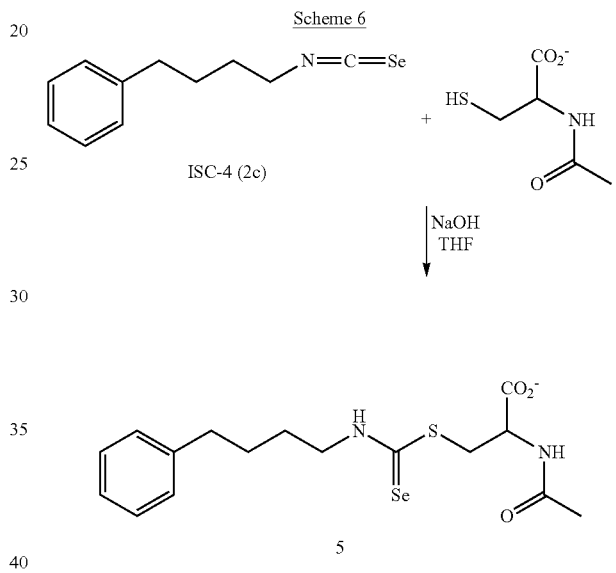

Example 10

1-isoselenocyanato-4-(methylsulfinyl)butane (ISC-SFN4, Also Called SFN Iso Se Herein)

viscous oil; $^1$H NMR in CDCl$_3$: 3.72 (t, 2H, J=6.53 Hz, N—CH$_2$), 3.10 (t, 2H, J=6.94 Hz, SO—CH$_2$), 2.97 (s, 3H, S—CH$_3$), 1.98-2.07 (m, 4H, C—CH$_2$—CH$_2$—C).

Example 11

IC$_{50}$ Values of ITC and ISC Compounds

To measure the inhibitory potency (IC$_{50}$) of isothiocyanate and isoselenocyanate derivatives in various cancer cells, MTS (CellTiter 96 Aqueous Non Radioactive Cell Proliferation Assay kit, Promega, Madison, Wis.) is used. Cellular viability is quantified by MTS assay and dose response curves plotted. $5 \times 10^3$ melanoma cells (UACC 903, 1205 LU or WM115) cells per well in 100 μL, DMEM containing 10% FBS are grown in a 96-well plate for 24 h and then treated with increasing concentrations of the indicated isothiocyanate or isoselenocyanate for 24 h. After 24 hours of treatment viable cells are measured by reading soluble colored formazan product at 490 nm using a microplate reader. Results of 3 independent experiments are considered for the determination of $IC_{50}$. The $IC_{50}$ values are calculated from the concentration curves using Graph Pad Prism software and are shown in Table I for cells and compounds indicated.

TABLE I

| | $IC_{50}$ (μM) 24 h drug treatment | | | | | | | |
|---|---|---|---|---|---|---|---|---|
| Cell Line | BITC | PEITC | PBITC | PHITC | ISC-1 | ISC-2 | ISC-4 | ISC-6 |
| UACC 903 | 15 ± 3 | 12 ± 1 | 15 ± 1 | 15 ± 2 | 16 ± 3 | 12 ± 4 | 12 ± 3 | 10 ± 1 |
| 1205 Lu | >25 | 24 ± 2 | 19 ± 5 | 11 ± 4 | >25 | 18 ± 4 | 11 ± 1 | 7 ± 4 |
| WM 115 | 13 ± 1 | 12 ± 1 | 7 ± 1 | 8 ± 1 | >25 | 8 ± 1 | 7 ± 2 | 7 ± 2 |

Table I shows a comparison of the $IC_{50}$ of isothiocyanates and isoselenocyanates in three independently derived melanoma cell lines, UACC 903, 1205 Lu and WM115. A general trend is observed in which increasing carbon chain length and substitution of selenium for sulfur decreased the $IC_{50}$. Increased potency ranged from 30-70% with increasing chain length and/or sulfur substituted for selenium. Thus, isothiocyanate analogs with longer alkyl chain lengths and sulfur substituted for selenium are better inhibitors of cultured melanoma cells.

Example 12

SAR Study on Cancer Cell Lines

Certain ITCs (1) and the corresponding ISCs (2) are tested for their ability to inhibit cell growth in five cancer cell lines e.g. melanoma, breast, glioblastoma, fibrosarcoma, colon and prostate cancers. In vitro inhibitory efficacy of cancer cell lines representing different cancer types following treatment with ITC and ISC is measured using the 3-(4,5-dimethylthiazol-2-yl)-5-(3-carboxymethoxyphenyl)-2-(4-sulfophenyl)-2H-tetrazolium (MTS) assay (Promega, Madison, Wis.). In brief, $2.5-5\times10^3$ cells per well in 100 μL DMEM containing 10% FBS are grown in a 96-well plate for 24 h and treated with either control DMSO vehicle or increasing concentrations (2.5-100 μM) of ITC and ISC for 24 hours. At this point cells are treated individually with either vehicle control DMSO or with increasing concentrations of ITC or ISC (2.5-100 μM) for 24 h. The percentages of viable cells compared to control DMSO treated cells are determined using MTS assay and $IC_{50}$ values calculated using GraphPad Prism version 4.01 (GraphPad software, San Diego, Calif.). $IC_{50}$ value for each compound was determined by at least three independent experiments and represented with a standard error (Table II).

The $IC_{50}$ values for compounds 1 and 2 are depicted in Table II. The values consistently decreased with increasing alkyl chain length of ITCs in case of MDA-MB-231, T98G, and PC-3 cell lines; but showed no particular trend in case of HT-1080, Caco-2, and UACC 903 cells. ISC-1 was least effective in killing cells in all the cell lines tested compared to its higher alkyl chain analogs ISC-2 to ISC-6. Among ISC-2, ISC-4 and ISC-6 there was no particular trend. The values generally decreased with increasing chain length for all the cancer cell lines tested except breast cancer cells MDA-MB 231 in case of ISC compounds and sarcoma HT 1080 cells in case of ITCs. Except for ISC-1 and ISC-2 in UACC 903 cells, the ISC derivatives had lower $IC_{50}$ values than corresponding ITCs.

TABLE II

| | $IC_{50}$ (μM) of ITC and ISC derivatives on different cancer cells | | | | | |
|---|---|---|---|---|---|---|
| | Cancer cell lines $IC_{50}$ (μM) | | | | | |
| Compounds | Breast MDA-MB-231 | Glioblastoma T-98-G | Prostate PC-3 | Fibrosarcoma HT-1080 | Colon Caco-2 | Melanoma UACC 903 |
| 1a (BITC) | 42 ± 3 | >100 | >50 | >50 | 15 ± 2 | 15 ± 3 |
| 1b (PEITC) | 38 ± 6 | >100 | 24 ± 2 | 15 ± 1 | 14 ± 2 | 12 ± 1 |
| 1c (PBITC) | 27 ± 2 | 35 ± 1 | 24 ± 2 | 15 ± 1 | 27 ± 2 | 15 ± 1 |
| 1d (PHITC) | 24 ± 2 | 26 ± 2 | 17 ± 1 | 29 ± 3 | 49 ± 9 | 15 ± 1 |
| 2a (ISC-1) | 29 ± 2 | 43 ± 4 | 24 ± 1 | 13 ± 3 | 13 ± 3 | 16 ± 3 |
| 2b (ISC-2) | 20 ± 3 | 24 ± 1 | 16 ± 1 | 12 ± 3 | 11 ± 1 | 12 ± 4 |
| 2c (ISC-4) | 21 ± 64 | 27 ± 1 | 19 ± 1 | 11 ± 1 | 12 ± 3 | 12 ± 3 |
| 2d (ISC-6) | 22 ± 2 | 23 ± 2 | 14 ± 1 | 12 ± 1 | 10 ± 1 | 10 ± 1 |

Values are mean ± S.E.
* Drug treatment for 72 h

Log P values are estimated for isothiocyanates and isoselenocyanates using ChemDraw 9.0 Ultra and these values are compared in Table III.

TABLE III

| ITCs | CLogP | ISCs | CLogP |
|---|---|---|---|
| 1a (BITC) | 3.204 | 2a (ISC-1) | 3.177 |
| 1b (PEITC) | 3.263 | 2b (ISC-2) | 3.506 |
| 1c (PBITC) | 4.171 | 2c (ISC-4) | 4.414 |
| 1d (PHITC) | 5.229 | 2d (ISC-6) | 5.472 |

[a]LogP was estimated using ChemDraw 9.0 Ultra

Example 13

Cell viability of melanoma cells following treatment with isothiocyanate or an isoselenocyanate is measured using the 3-(4,5-dimethylthiazol-2-yl)-5-(3-carboxymethoxyphenyl)-2-(4-sulfophenyl)-2H-tetrazolium (MTS) assay (Promega, Madison, Wis.).

Briefly, $5 \times 10^3$ melanoma cells (UACC 903, 1205 LU or WM115) or human fibroblast (FF2441) cells per well in 100 µL DMEM containing 10% FBS are grown in a 96-well plate for 24 h and treated with either control DMSO vehicle; phenylhexyl selenocyanate (PHSC), used as a control compound since it is similar to ISC-6 in structure and contains selenium; API-2, an Akt inhibitor used for comparison purposes; or increasing concentrations (2.5-50 µM) of an isothiocyanate or an isoselenocyanate for 24 h. Cellular viability compared to control treated cells is measured using the MTS assay. $IC_{50}$ values for each compound in respective cell lines is determined from three independent experiments using GraphPad. Prism version 4.01 (GraphPad software, San Diego, Calif.).

Figure 1B:
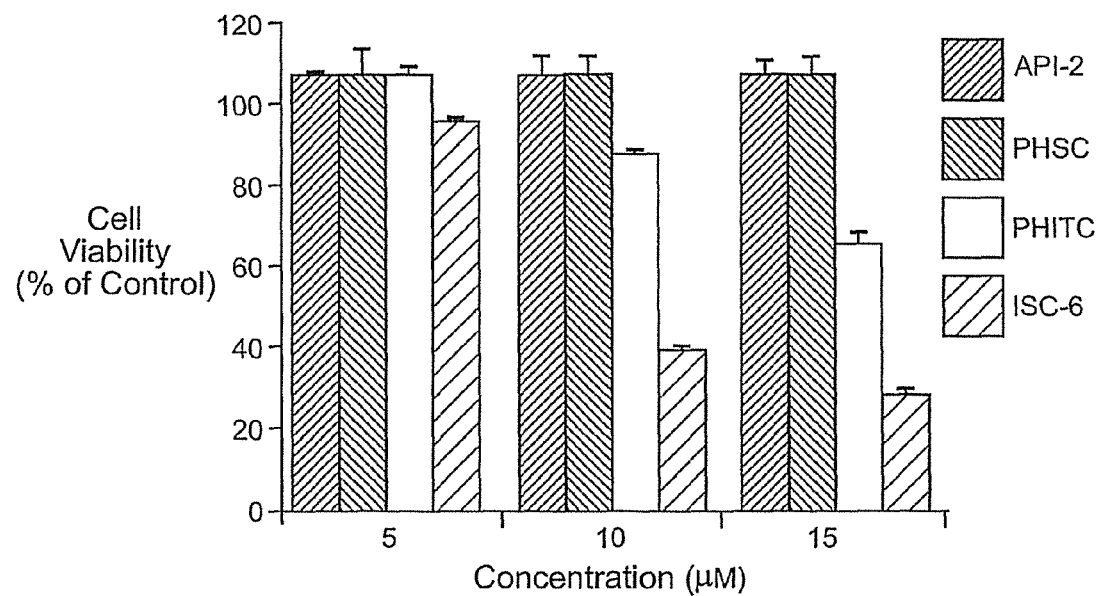
FIG. 1B is a bar graph showing a comparison of cell viability following exposure to PHITC or ISC-6, compared to controls.

FIG. 1A shows a comparison of cell viability following exposure to PBITC or ISC-4, compared to controls. FIG. 1B shows a comparison of cell viability following exposure to PHITC or ISC-6, compared to controls. Cell viability is determined using MTS assay. ISC-4 effectively reduces cell viability at concentrations of 10 µM and 15 µM ($IC_{50}$=12±3 and 10±1 µM) compared to controls (API-2, PHSC) or PBITC or PHITC ($IC_{50}$=15±1 and 15±2 µM). The average value represented as the percentage of control DMSO treated cells. Phenylhexyl selenocyanate (PHSC) is used as a control compound since it is similar to ISC-6 in structure and contains selenium. API-2 is an Akt inhibitor used for comparison purposes. Thus, ISC-4 and ISC-6 are more effective at inhibiting growth of melanoma cells than sulfur containing PBITC, PHITC, control PHSC or API-2.

Example 14

Cellular proliferation in vitro is measured by seeding $5 \times 10^3$ cells in 96-well plate, followed by treatment for 24 hours with vehicle control DMSO, or 5 µM, 10 µM or 15 µM of API-2 (a known Akt inhibitor), PHSC, PBITC, PHITC, ISC-4, or ISC-6. Proliferation rate is measured using a BrdU ELISA kit (Roche Applied Sciences, Indianapolis, Ind.).

Figure 2A:
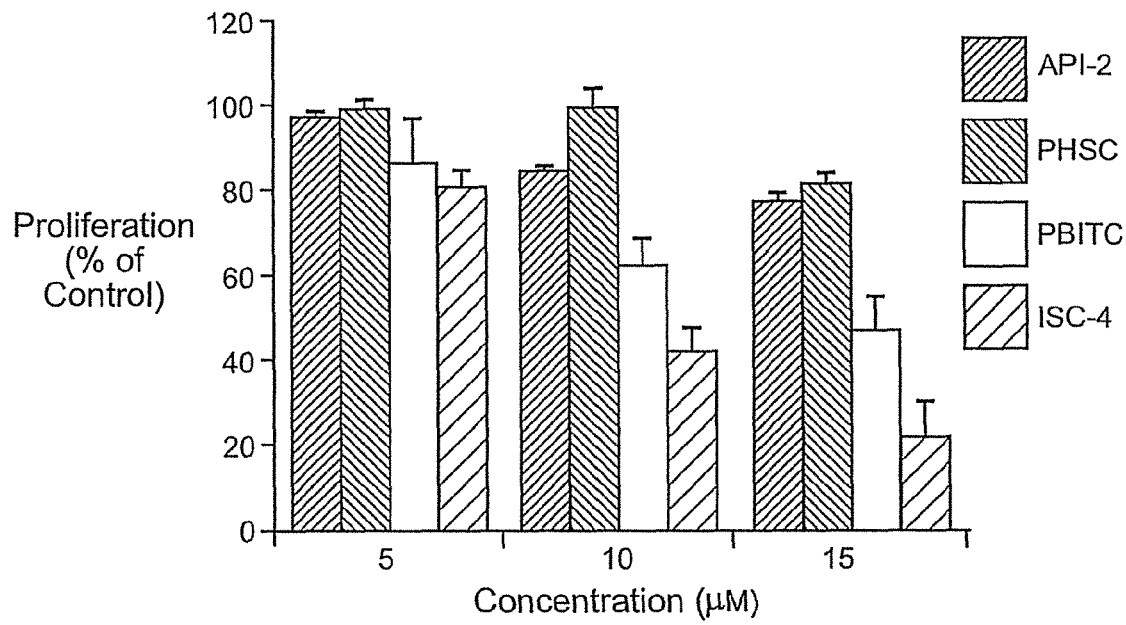
FIG. 2A is a bar graph of results of proliferation analysis of UACC 903 cells treated with DMSO or different concentrations (5 uM, 10 uM, 15 uM) of API-2, PHSC, PBITC or ISC-4 for 24 hours.
Figure 2B:
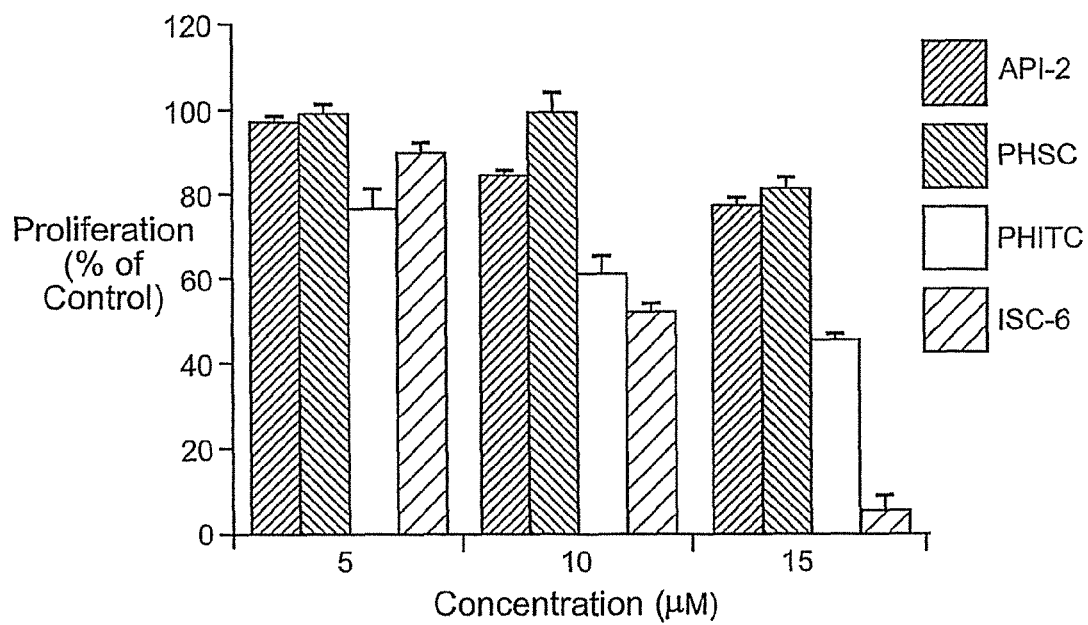
FIG. 2B is a bar graph of results of proliferation analysis of UACC 903 cells treated with DMSO or different concentrations (5 uM, 10 uM, 15 uM) of API-2, PHSC, PHITC or ISC-6 for 24 hours.

FIG. 2A shows results of proliferation analysis of UACC 903 cells treated with DMSO or different concentrations (5 uM, 10 uM, 15 uM) of API-2, PHSC, PBITC or ISC-4 for 24 hours. FIG. 2B shows results of proliferation analysis of UACC 903 cells treated with DMSO or different concentrations (5 uM, 10 uM, 15 uM) of API-2, PHSC, PHITC or ISC-6 for 24 hours. BrdUrd is used to label cells for 4-6 hours. At 15 µM concentration, ISC-4 and ISC-6 reduced UACC 903 cellular proliferative potential by ~80-90% compared to controls. Results represent the average of 3 independent experiments; bars represent SEM. The average value is represented as the percentage of control DMSO treated cells.

In contrast to the Akt inhibitor API-2 or the control 6-carbon selenium compound PHSC, increasing concentrations of PBITC, ISC-4, PHITC or ISC-6 led to decreased proliferative potential of treated cells. Both ISC-4 and ISC-6 are ~2-fold more effective than PBITC or PHITC at inhibiting cellular proliferation.

Example 15

Apoptosis rates are measured by seeding $5 \times 10^3$ cells in 96-well plate, followed by treatment for 24 hours with vehicle control DMSO; API-2; PHSC; PBITC; PHITC; ISC-4; or ISC-6. Apoptosis rates are measured using an Apo-ONE Homogenous caspase-3/7 Assay kit (Promega Corporation, Madison, Wis.).

Figure 3A:
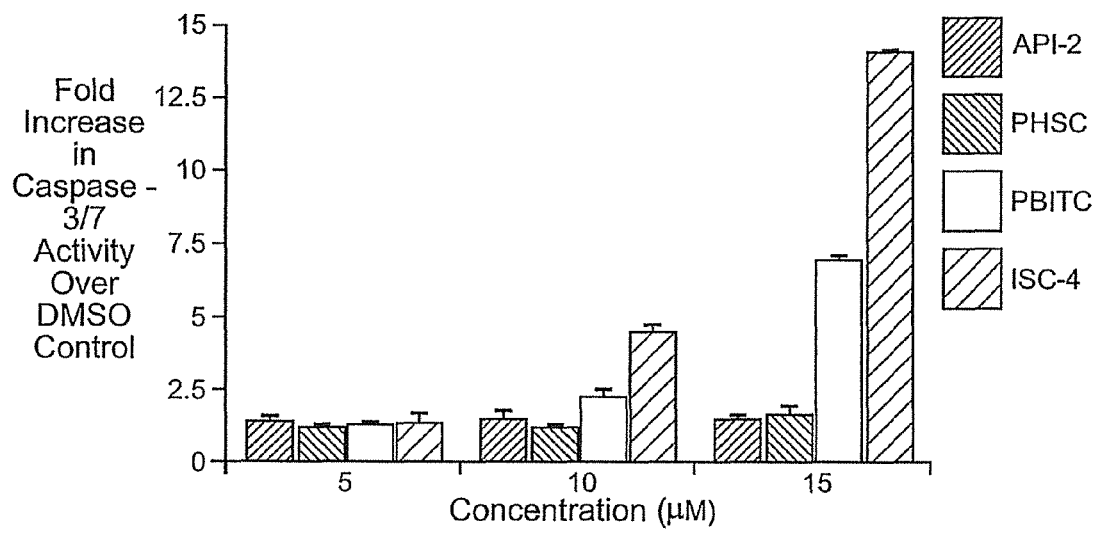
FIG. 3A is a bar graph showing the effects of treatment of UACC 903 cells in culture with DMSO or 5 μM, 10 μM or 15 μM of API-2, PHSC, PBITC or ISC-4 for 24 hours on caspase-3/7 activity, an indicator of apoptosis.
Figure 3B:
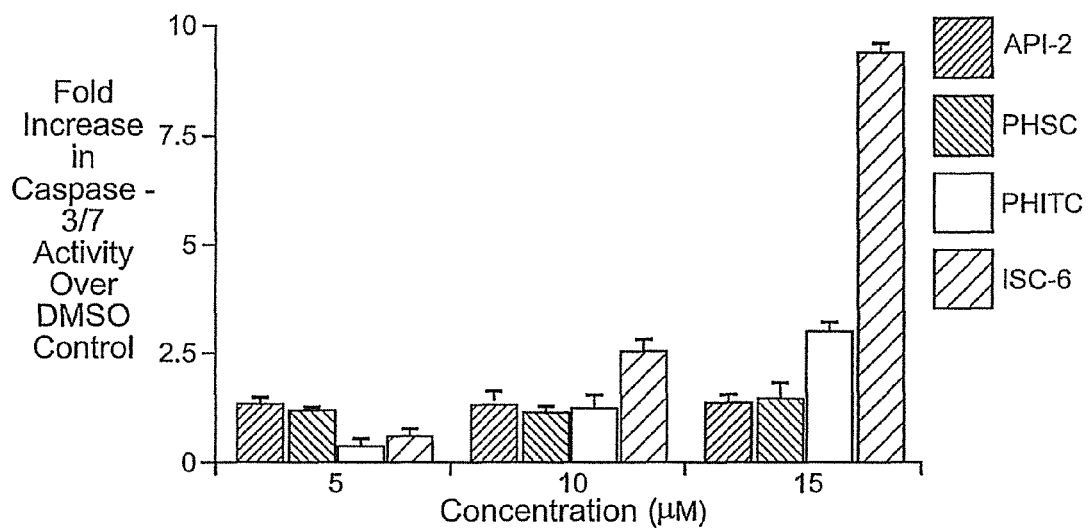
FIG. 3B is a bar graph showing the effects of treatment of UACC 903 cells in culture with DMSO or 5 μM, 10 μM or 15 μM of API-2, PHSC, PHITC or ISC-6 for 24 hours on caspase-3/7 activity, an indicator of apoptosis.

FIG. 3A shows the effects of treatment of UACC 903 cells in culture with DMSO or 5 µM, 10 µM or 15 µM of API-2, PHSC, PBITC or ISC-4 for 24 hours on caspase-3/7 activity, an indicator of apoptosis. FIG. 3B shows the effects of treatment of UACC 903 cells in culture with DMSO or 5 µM, 10 µM or 15 µM of API-2, PHSC, PHITC or ISC-6 for 24 hours on caspase-3/7 activity, an indicator of apoptosis. The isoselenocyanate compounds promote apoptosis in melanoma cells. Levels of caspase-3/7 activity in cells exposed to API-2, PHSC, PBITC, PHITC, ISC-4 or ISC-6 are measured using the Apo-ONE homogeneous caspase-3/7 assay kit. The graphs in FIGS. 3A and 3B show fold increase in caspase-3/7 activity relative to DMSO vehicle treated cells on the x-axis. Results represent average of 3 independent experiments. Bars indicate SEM. In contrast to API-2 and PHSC, increasing concentrations of PBITC, ISC-4, PHITC and ISC-6 increase cellular apoptosis of UACC 903 melanoma cells as shown in FIGS. 3A and 3B. ISC-4 and ISC-6 are ~2-fold more effective than PBITC at inducing apoptosis.

Example 16

Cell cycle analysis is performed by plating $1.5 \times 10^6$ melanoma cells in 100-mm culture dish. Two days following plating, cells are treated with DMSO, or 5 µM, 10 µM or 15 µM of API-2, PHSC, PBITC, PHITC, ISC-4, or ISC-6 for 24 hours. Cells are collected by trypsinization and stained using propidium iodide (13). Trypsinized cells are centrifuged (500×g, for 5 minutes) and treated with 1 mL of propidium iodide staining solution (100 µg/mL; Sigma, St Louis, Mo.), 20 µg/mL Ribonuclease A (Roche Applied Sciences, Indianapolis, Ind.) 3 µg/mL Triton X-100 dissolved in 0.1% (W/V) sodium citrate for 30 minutes at 4° C. Stained cells are analyzed using the FACScan analyzer (Becton Dickinson, San Jose, Calif.) and data analyzed using ModFit LT software (Verity Software House, Topsham, Me.).

Figure 4A:
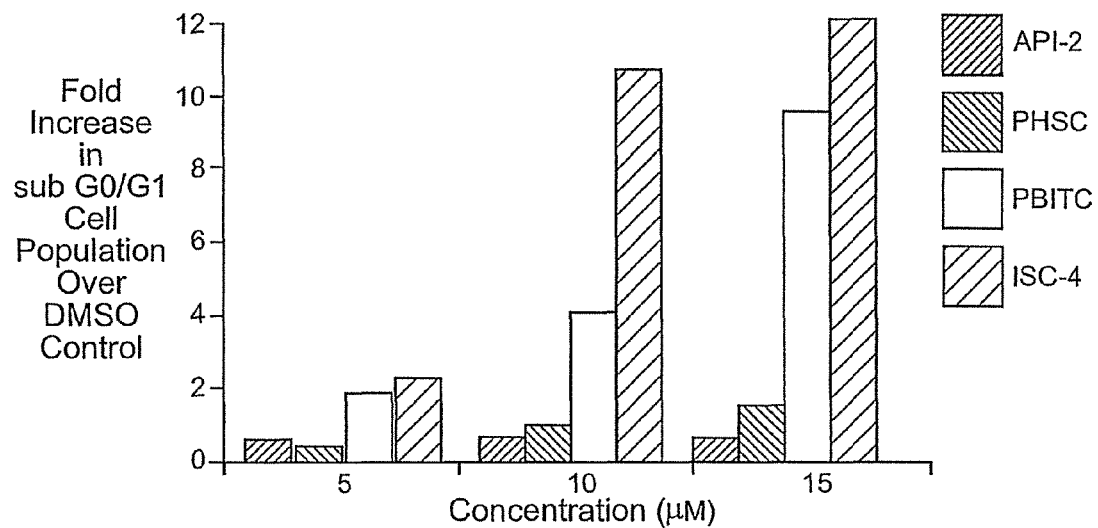
FIG. 4A is a bar graph showing results of cell cycle analysis of UACC 903 cells treated with controls (API-2, PHSC), PBITC or ISC-4.
Figure 4B:
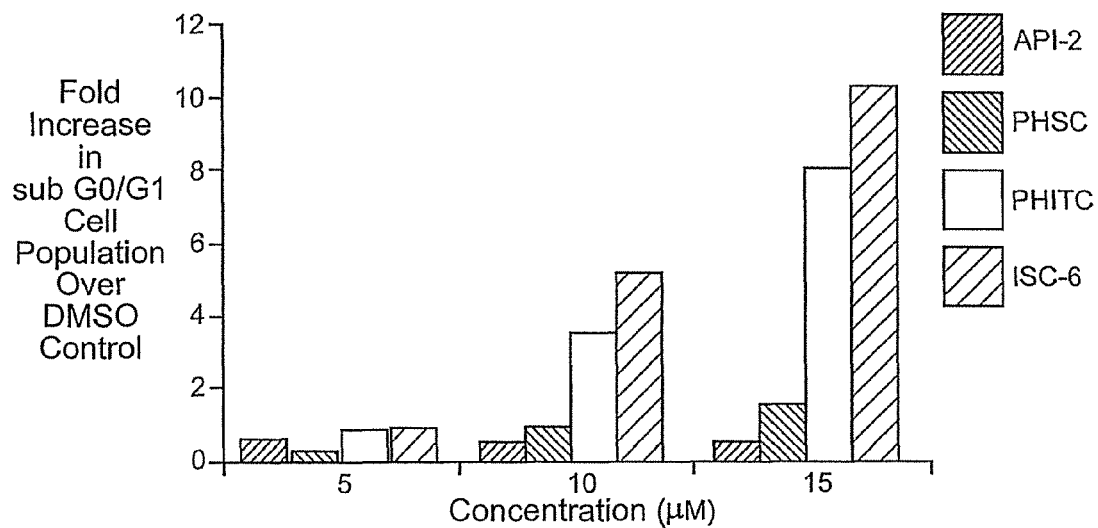
FIG. 4B is a bar graph showing results of cell cycle analysis of UACC 903 cells treated with controls (API-2, PHSC), PHITC or ISC-6.

FIG. 4A shows results of cell cycle analysis of UACC 903 cells treated with controls (API-2, PHSC), PBITC or ISC-4, or, DMSO vehicle control. FIG. 4B shows results of cell cycle analysis of UACC 903 cells treated with controls (API-2, PHSC), PHITC or ISC-6, or, DMSO vehicle control. ISC-4, ISC-6, PBITC or PHITC treatment increased the sub G0/G1 cell population (an indicator of apoptosis) and induces G2/M cell cycle arrest in melanoma cells compared to DMSO or controls API-2 and PHSC. Results represent average of 2 independent experiments. Enhanced apoptosis induced by ISC-4 or ISC-6 is confirmed through cell cycle analysis of asynchronously growing UACC 903 cells. A significant increase is observed in the sub G0/G1 population in PBITC, ISC-4, PHITC or ISC-6 treated cells which is indicative of cells undergoing apoptosis.

Table IV shows results of cell cycle analysis following treatment with controls compounds DMSO, API-2 or PHSC or test compounds PBITC, PHITC, ISC-4 or ISC-6. Treated cells are stained with propidium iodide and cell cycle analyzed using a FACScan analyzer such that the proportion of cells in each phase of cell cycle (G0/G1, S, G2/M) is estimated. The G2/M cell population increases 2-3 fold following 15 µM PBITC, PHITC, ISC-4 or ISC-6 exposure. A significant decrease in G0/G1 cell population occurred following ITC or ISC treatment. Enhanced apoptosis induced by ISC-4 or ISC-6 is confirmed through cell cycle analysis of asynchronously growing UACC 903 cells. Analysis of cells in each stage of the cell cycle showed decreasing numbers of cells in the S— and G1/G0 phase with a corresponding increase in the G2/M phase.

TABLE IV

UACC 903 - Cell Cycle Analysis Following Treatment With ISC-4 or ISC-6 and Corresponding Isothiocyanates

| | DMSO | API-2 | PHSC | PBITC | | | ISC-4 | | | PHITC | | | ISC-6 | | |
|---|---|---|---|---|---|---|---|---|---|---|---|---|---|---|---|
| | | | | | | | Concentration (μM) | | | | | | | | |
| | | 15 | 15 | 5 | 10 | 15 | 5 | 10 | 15 | 5 | 10 | 15 | 5 | 10 | 15 |
| subG0/G1 | 0.4 | 0.89 | 2.4 | 4.9 | 10.4 | 20.8 | 2.9 | 12.3 | 22.8 | 1.4 | 5.4 | 12.5 | 1.5 | 7.6 | 15.9 |
| G0/G1 | 60.8 | 63.6 | 61.4 | 37.4 | 37.2 | 42.1 | 59.4 | 41.6 | 35.5 | 58.7 | 43.8 | 40.7 | 56.8 | 44.9 | 41.6 |
| S | 27.7 | 25.6 | 26.9 | 27.8 | 30.9 | 30.5 | 24.3 | 29.0 | 36.5 | 28.2 | 28.7 | 29.6 | 31.5 | 30.5 | 32.2 |
| G2/M | 11.4 | 10.7 | 11.5 | 34.7 | 31.9 | 27.4 | 16.3 | 29.4 | 28.0 | 13.1 | 27.5 | 29.7 | 13.5 | 24.5 | 26.1 |

Example 17

Isoselenocyanates are effective for inhibiting melanoma tumor development in preexisting tumors in nude mice.

Tumor kinetics are measured by subcutaneous injection of 2.5–5×10$^6$ 1205 Lu or UACC 903 melanoma cells in 0.2 ml of DMEM supplemented with 10% FBS above both left and right rib cages of 4-6 week old female nude mice (Harlan Sprague Dawley, Indianapolis, Ind.). Six days later when a fully vascularized tumor has formed, mice are randomly divided into DMSO vehicle control and experimental groups including 5 mice/group, each mouse having two tumors. Mice are treated by intraperitoneal (i.p.) injection with an ITC compound BITC, PEITC, PBITC, or PHITC (2.5 μmoles or 0.76 μmoles); or treated by i.p injection with an ISC compound ISC-1-ISC-2, ISC-4 or ISC-6 (0.76 μmoles, equivalent to 3 ppm selenium) thrice per week. (Monday, Wednesday and Friday). Control mice received an equal volume of the vehicle. Dimensions of the developing tumors are measured using calipers and the size estimated in cubic millimeters. Body weight is monitored three times a week (Monday, Wednesday and Friday).

Figure 5A:
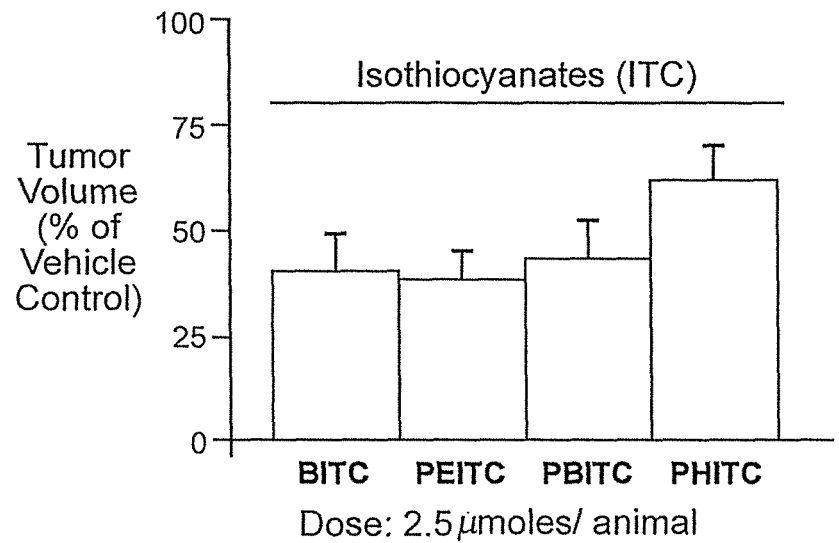
FIG. 5A is a bar graph showing the effect of isothiocyanates on tumor development.
Figure 5B:
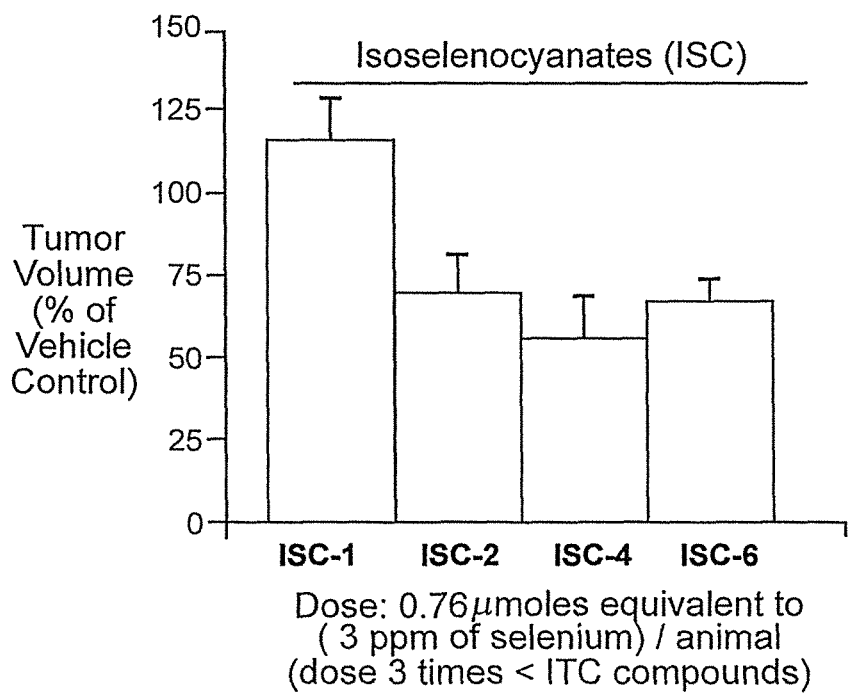
FIG. 5B is a bar graph showing the effect of isoselenocyanates on tumor development.

FIGS. 5A and 5B show graphs comparing the effect of isothiocyanates and isoselenocyanates on tumor development using UACC 903 melanoma cells, a cell line having high Akt3 signaling activity. Six days following subcutaneous injection of 5 million UACC 903 melanoma cells, small vascularized palpable tumors are seen and mice are treated i. p. with 2.5 moles of an isothiocyanate or with 0.76 μmoles, equivalent to 3 ppm selenium, of an isoselenocyanate thrice per week. The bar graphs in FIGS. 5A and 5B show melanoma tumor volume, as % of vehicle, at day 24. Isoselenocyanates ISC-2, ISC-4 and ISC-6 reduce tumor volume at doses 3× lower than isothiocyanates. ISC, 0.76 μmoles vs. ITC, 2.5 μmoles. Thus, isoselenocyanates have increased in vivo tumor inhibitory effectiveness compared to corresponding isothiocyanates and effectively reduce melanoma development. Increasing carbon chain length of isothiocyanates showed less effective tumor inhibition, FIG. 5A, while increasing carbon chain length of isoselenocyanates led to greater tumor inhibition, FIG. 5B.

Example 18

Isoselenocyanates Retard Melanoma Tumor Development

The effect of isothiocyanates and isoselenocyanates on tumor development is measured in existing tumors formed by subcutaneous injection of 2.5 or 5 million 1205 Lu or UACC 903 melanoma cells. Six days following injection of the cells, when small vascularized palpable tumors are seen, mice are treated i. p. with PBITC or PHITC (0.76 μmoles) or ISC-4 or ISC-6 (0.76 μmoles, equivalent to 3 ppm selenium) thrice per week.

Figure 6A:
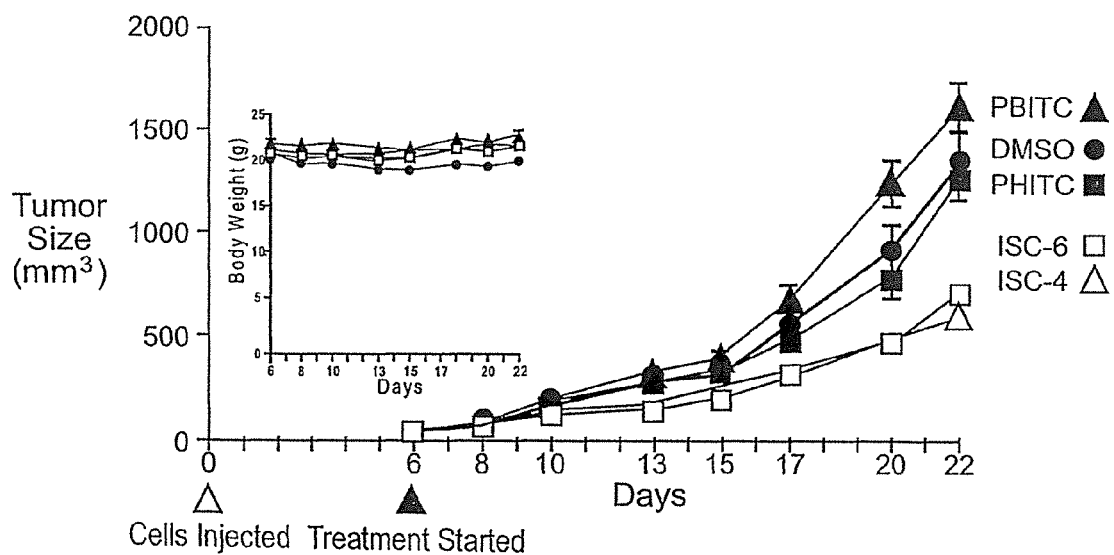
FIG. 6A is a line graph showing change in tumor size and body weight (inset) over time in mice treated i. p. with PBITC or PHITC (0.76 μmoles) or ISC-4 or ISC-6 (0.76 μmoles, equivalent to 3 ppm selenium)
Figure 6B:
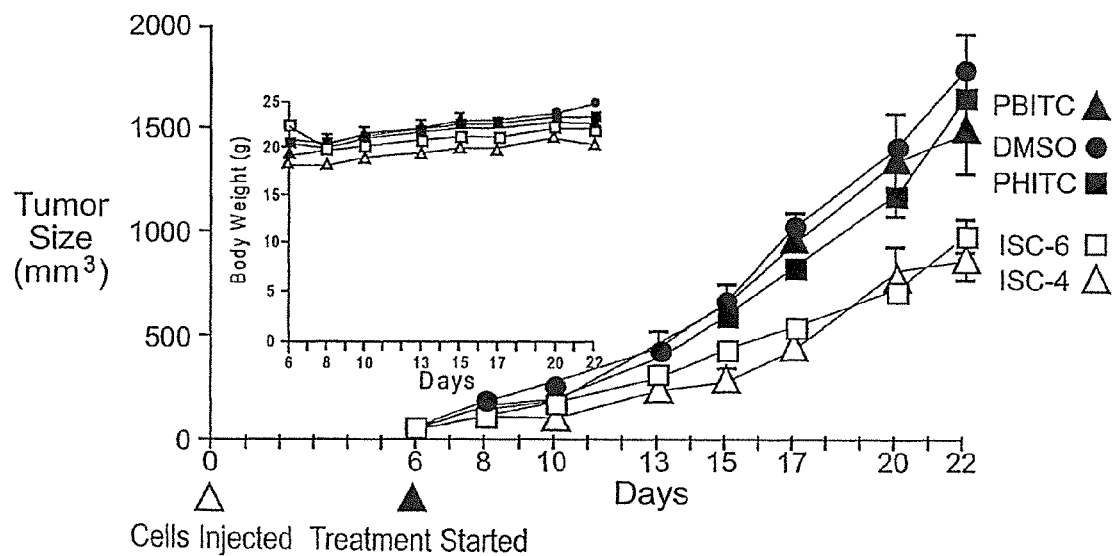
FIG. 6B is a line graph showing change in tumor size and body weight (inset) over time in mice treated i. p. with PBITC or PHITC (0.76 mmoles) or ISC-4 or ISC-6 (0.76 μmoles, equivalent to 3 ppm selenium)

FIGS. 6A and 6B show graphs of change in tumor size and body weight over time in mice treated i. p. with PBITC or PHITC (0.76 μmoles) or ISC-4 or ISC-6 (0.76 μmoles, equivalent to 3 ppm selenium) thrice per week. Selenium containing analogs ISC-4 or ISC-6 significantly reduced tumor development compared to DMSO, PBITC or PHITC controls. While PBITC and PHITC are ineffective at reducing tumor burden of UACC 903, FIG. 6A, or 1205 Lu, FIG. 6B, at the administered concentration of 0.76 μmoles, administration of 0.76 μmoles of ISC-4 or ISC-6 led to significant reductions of 50-60% in tumor size of both cell types. No obvious toxicity is observed by significant changes in body weight. Data are presented as mean±SE. Thus, isoselenocyanates (ISC) are effective at reducing melanoma tumor development at significantly lower concentrations than corresponding isothiocyanates (ITC).

Example 19

Measurement of Proliferation/Apoptosis Rates in Tumors

Tumors are established by subcutaneous injection of 2.5–5×10$^6$ 1205 Lu or UACC 903 melanoma cells in 0.2 ml of DMEM supplemented with 10% FBS above both left and right rib cages of 4-6 week old female nude mice (Harlan Sprague Dawley, Indianapolis, Ind.). Six days later when a fully vascularized tumor forms, mice are randomly divided in to DMSO vehicle control and experimental (BITC, PEITC, PBITC, PHITC, ISC-1-ISC-2, ISC-4 or ISC-6) groups (5 mice/group; 2 tumors/mouse) and treated i. p. with ITC compounds (2.5 μmoles or 0.76 μmoles), ISC compounds (0.76 μmoles, equivalent to 3 ppm selenium) thrice per week. (Monday, Wednesday and Friday). Control mice receive an equal volume of the vehicle. Dimensions of the developing tumors are measured using calipers and the size estimated in cubic millimeters. Body weight is monitored three times a week (Monday, Wednesday and Friday).

Isoselenocyanates decrease the tumorigenic potential of melanoma cells by increasing apoptosis.

Figure 7A:
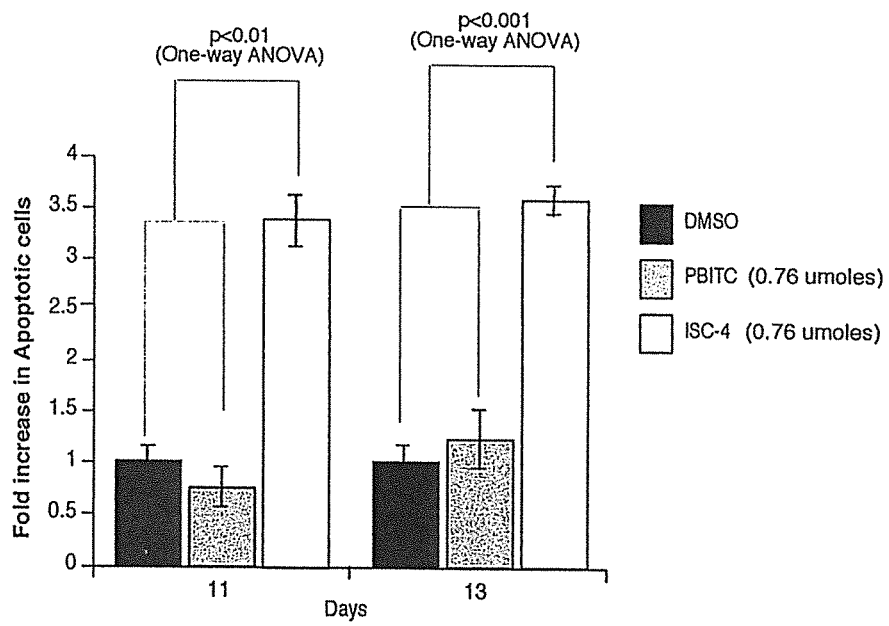
FIG. 7A is a bar graph showing results of analysis of apoptosis following ISC-4 treatment compared to treatment with PBITC or DMSO, in size and time matched tumors.

FIG. 7A shows that ISC treatment leads to apoptosis in size and time matched melanoma tumors. Mice bearing tumors matched for size and time of development are injected i. p. with PBITC (0.76 μmoles), ISC-4 (3 ppm equivalent to 0.76 μmoles) or DMSO (50 μl) vehicle starting 6 days after subcutaneous injection of cells and on alternate days thereafter up to day 15. Following ISC-4 treatment, rates of tumor cell apoptosis and cell proliferation are compared in size and time matched tumors from ISC-4 or PBITC treated animals compared to DMSO vehicle. Tumors are removed from euthanized mice on days 9, 11, 13, and 15 for measurement of apoptosis and proliferation. Apoptosis and cell proliferation are measured in formalin-fixed, paraffin-embedded tumor sections using the TUNEL TMR Red Apoptosis kit from Roche (Manheim, Germany) or purified mouse anti-human Ki-67 from PharMingen (San Diego, Calif.), respectively.

Tumors harvested at day 11 and 13 from mice treated with ISC-4 showed ~3-fold (p<0.01; One-way ANOVA) more TUNEL positive cells compared to control animals treated with DMSO or PBITC, as shown in FIG. 7A. In contrast, slightly fewer proliferating tumor cells are observed in ISC-4 treated tumors compared to PBITC but this difference is not statistically significant (p>0.05; One-way ANOVA), shown in FIG. 7B.

Figure 7B:
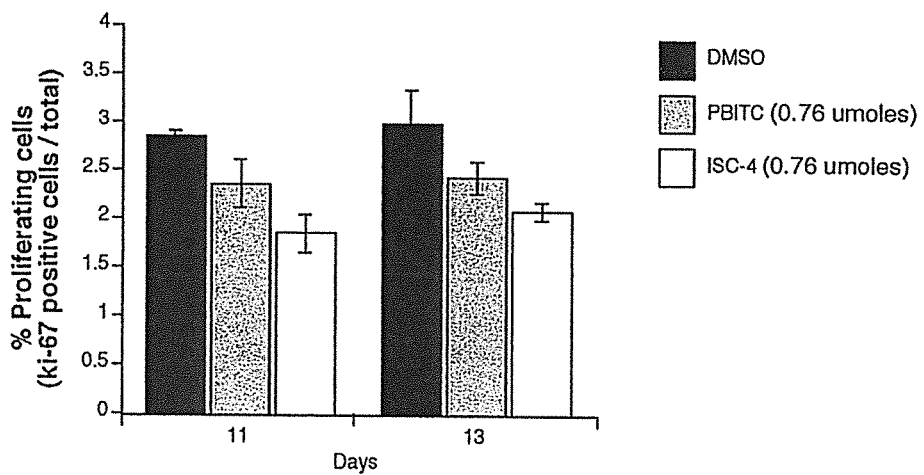
FIG. 7B is a bar graph showing results of analysis of cell proliferation following ISC-4 treatment compared to treatment with PBITC or DMSO, in size and time matched tumors.

A 3-fold increase in number of apoptotic cells is observed following treatment of UACC 903 tumors with ISC-4 at Day 11 and 13 respectively compared to PBITC or DMSO control. No significant changes are observed in rate of proliferation. Values shown in FIGS. 7A and 7B are means from 2 separate experiments with 4-6 fields analyzed from each of 6 tumors per experiment; bars, ±SEM. ISC-4 is more potent than PBITC in inhibiting melanoma tumor development by increasing apoptosis levels in melanoma tumors.

Example 20

Toxicity Assessments 4-6 weeks old female nude mice (Harlan Sprague Dawley, Indianapolis, Ind.) are injected i. p. with either control DMSO vehicle, PBITC or PHITC (0.76 μmoles) or ISC-4 or ISC-6 (0.76 μmoles equivalent to 3 ppm Se) (n=5), 3 times per week (Monday, Wednesday and Friday) for 3 weeks. Animals are sacrificed by $CO_2$ asphyxiation and blood collected from each animal in plasma separator tubes with lithium heparin (BD Microtainer, BD, Franklin Lakes, N.J.) following cardiac puncture and analyzed for AST (aspartate aminotransferase), ALT, (alanyl aminotransferase), alkaline phosphatase, glucose and creatinine to ascertain liver, heart, kidney and pancreas related toxicity. For morphological examination of blood cells, whole blood is collected in microtainer tubes containing $K_2$EDTA (BD Microtainer, BD, Franklin Lakes, N.J.) and RBC, WBC, lymphocytes, monocytes, eosinophils, platelets, total hemoglobin and hematocrit percentage analyzed. Blood is also microscopically examined for segregates, polychromatin bodies, and smudge cells. A portion of liver, heart, kidney, spleen, intestine pancreas and adrenal from each animal is formalin fixed and paraffin-embedded to examine toxicity-related changes in cell or organ morphology by H&E staining.

Body weights of isothiocyanate or isoselenocyanate treated mice compared to the control DMSO vehicle exposed mice showed no significant differences between groups as shown in the two graph inserts in FIGS. 6A and 6B.

Figure 8:
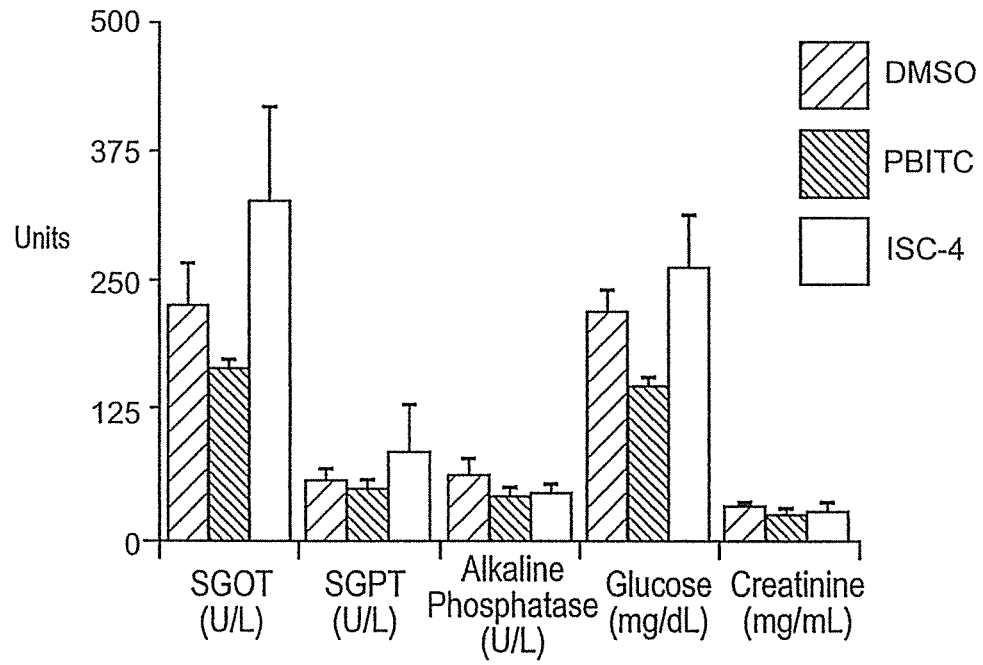
FIG. 8 is a bar graph showing results of analysis of levels of SGOT, SGPT, alkaline phosphatase, glucose and creatinine in blood collected from animals treated with PBITC, ISC-4 or DMSO vehicle.

Levels of SGOT, SGPT, alkaline phosphatase, glucose and creatinine are analyzed in the blood collected from the animals treated with PBITC, ISC-4 or DMSO vehicle. FIG. 8 shows a bar graph indicating that synthetic isoselenocyanates have negligible toxicity and treatment with PBITC or ISC-4 did not alter parameters compared to vehicle DMSO treated animals indicating manageable toxicity to vital organs with these agents.

Furthermore, blood parameters (SGOT, SGPT, alkaline phosphatase, blood urea, glucose and creatinine) indicative of systemic toxicity did not detect significant liver, kidney or cardiac related toxicity. Levels of cellular metabolites basal urea nitrogen (BUN), creative and glucose in animals are also not significantly different between ISC-4 or PBITC treated and control animals. Histological examination of hematoxylin and eosin stained vital organ sections, including the liver reveal that ISC-4 treatment did not significantly change cell morphology or organ structure. Thus, synthetic selenium containing analog isothiocyanate treatment had negligible associated systemic toxicity at the concentrations examined with significant therapeutic potential. Synthetic isoselenocyanate compounds cause negligible organ related toxicity following systemic administration.

Example 21

Statistical Analysis

Statistical analysis is undertaken using the One-way or Two-way ANOVA followed by the Tukey's or Bonferroni's post hoc tests. Results are considered significant at a p-value of <0.05.

Example 22

Western Blot Analysis of Melanoma Cells Treated with Isoselenocyanates ISC-4 and ISC-6

For Western blot analysis, floating and attached melanoma cells treated with compounds or control vehicle are harvested by addition of lyses buffer containing 50 mM HEPES (pH 7.5), 150 mM NaCl, 10 mM EDTA, 10% glycerol, 1% Triton X-100, 1 mM sodium orthovanadate, 0.1 mM sodium molybdate, 1 mM phenylmethylsulfonyl fluoride, 20 μg/ml aprotinin, and 5 μg/ml leupeptin. Whole cell lysates are centrifuged (≥10,000×g) for 10 minutes at 4° C. to remove cell debris. Protein concentrations are quantitated using the BCA assay from Pierce (Rockford, Ill.), and 30 μg of lysate loaded per lane onto NuPAGE Gels from Life Technologies (Carlsbad, Calif.). Following electrophoresis, samples are transferred to polyvinylidene difluoride membrane (Pall Corporation, Pensacola, Fla.). Blots are probed with antibodies according to each supplier's recommendations: phosphorylated PRAS40 (Thr246) from Invitrogen (Carlsbad, Calif.); Erk2, α-enolase and secondary antibodies conjugated with horseradish peroxidase from Santa Cruz Biotechnology (Santa Cruz, Calif.); and antibodies to Akt3, phosphorylated-Akt (Ser473), phosphorylated-Erk 1/2 (Thr202/Tyr204) and cleaved PARP from Cell Signaling Technology (Danvers, Mass.). Immunoblots are developed using the enhanced chemiluminescence detection system (Pierce Biotechnology, Rockford, Ill.).

Figure 9:
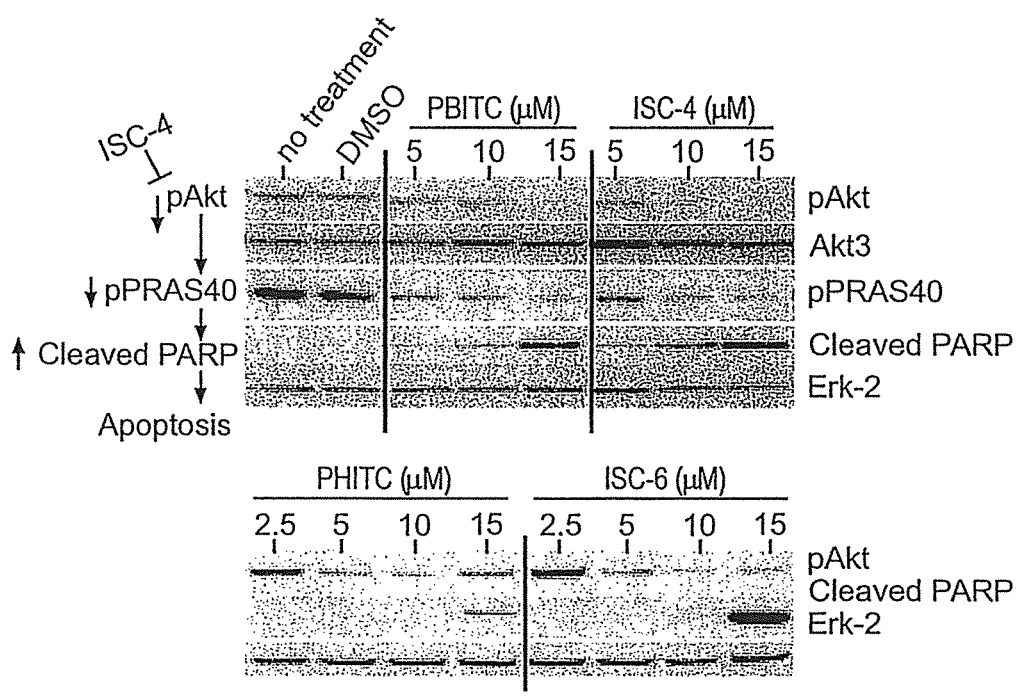
FIG. 9 is a reproduction of an image of an immunoblot showing dose dependent decreases in phosphorylated (active) Akt (S473) and downstream PRAS40 (T246) and a corresponding dose dependent increase in cleaved PARP, reflective of high levels of cellular apoptosis in cells treated with ISC-4 or ISC-6.

Melanoma cells (UACC 903, 1205 Lu or WM 115) are exposed to DMSO or increasing concentrations (2.5-15 μM) of phenylbutylisothiocyanate (PBITC), phenylhexylisothiocyanate (PHITC), phenylbutylisoselenocyanate (ISC-4) or phenylhexylisoselenocyanate (ISC-6) for 24 hours. FIG. 9 shows a representative Western blot analysis for expression/activity of the Akt signaling pathway and demonstrates dose dependent decrease in phosphorylated (active) Akt (S473) and downstream PRAS40 (T246) and a corresponding dose dependent increase in cleaved PARP, reflective of high levels of cellular apoptosis. A higher level of apoptosis is observed in cells treated with ISC-4 than in cells treated with PBITC. Erk2 served as control for equal protein loading. Isoselenocyanates decrease Akt3 signaling in cultured melanoma cells and tumors.

The Western blot in FIG. 9 shows that the isoselenocyanate compounds ISC-4 and ISC-6 are effective at lower concentrations compared to the isothiocyanate compounds, completely inhibiting the pathway at 10 μM compared to corresponding isothiocyanates requiring ≥15 μM for similar inhibition. Akt3 pathway inhibition led to significant apoptosis as measured by the high levels of cleaved PARP. Higher levels of cleaved PARP are observed at lower concentrations of ISC-4 and ISC-6 than corresponding isothiocyanates PBITC or PHITC.

Figure 10:
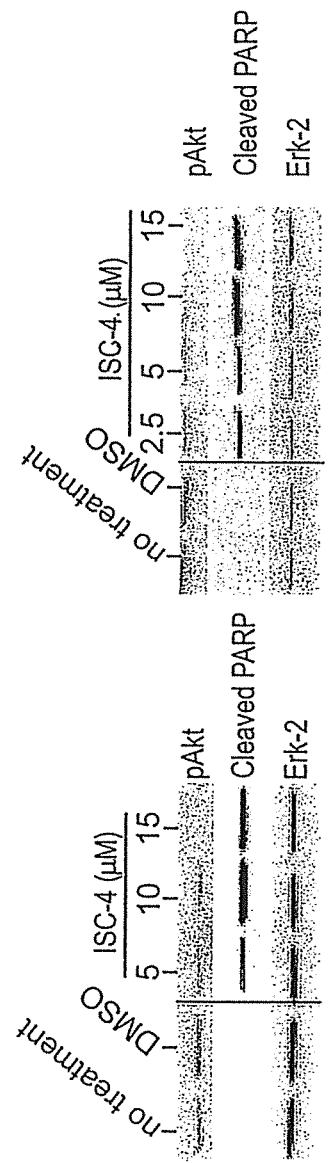
FIG. 10A is a reproduction of an image of an immunoblot showing the effect of ISC-4 on Akt signaling pathway in melanoma cell line 1205 Lu.
FIG. 10B is a reproduction of an image of an immunoblot showing the effect of ISC-4 on Akt signaling pathway in melanoma cell line WM115.

FIGS. 10A and 10B illustrate Western blots showing the effect of ISC-4 on Akt signaling pathway in melanoma cell lines 1205 Lu and WM115, respectively. ISC-4 causes significant apoptosis indicated by elevated cleaved PARP protein levels. Erk-2 served as a control for equal protein loading.

Thus, isoselenocyanates ISC-4 and ISC-6 more effectively inhibit the Akt3 signaling cascade in cultured melanoma cells at lower concentrations than corresponding sulfur containing isothiocyanates.

Example 23

Western Blot Analysis of Excised Tumors

To ascertain the mechanism underlying tumor inhibition, 5×10⁶ UACC 903 cells are injected into nude mice, 6-days later mice are treated i. p. with PBITC (0.76 μmoles) or PHITC (0.76 μmoles), ISC-4 (0.76 μmoles, equivalent to 3 ppm selenium) or ISC-6 (0.76 μmoles, equivalent to 3 ppm selenium) on alternate days. Size and time matched tumors are harvested at days 9, 11 and 13 and a small portion of the tumor is flash frozen in liquid nitrogen, pulverized and lysed in protein lysis buffer (600-800 μl, 50 mM Tris-HCl, pH 7.5 containing 0.1% Triton X-100, 1 mM EDTA, 1 mM EGTA, 50 mM sodium fluoride, 10 mM sodium β-glycerol phosphate, 5 mM sodium pyrophosphate, 1 mM activated sodium orthovanadate, protease inhibitor cocktail from Sigma and 0.1% (v/v) 2-mercaptoethanol). Protein concentration is determined using Bio-Rad protein assay reagent (Bio-Rad laboratories, Hercules, Calif.) and analyzed by Western blotting to measure levels of pAkt and downstream pPRAS40 in tumors.

Figure 11:
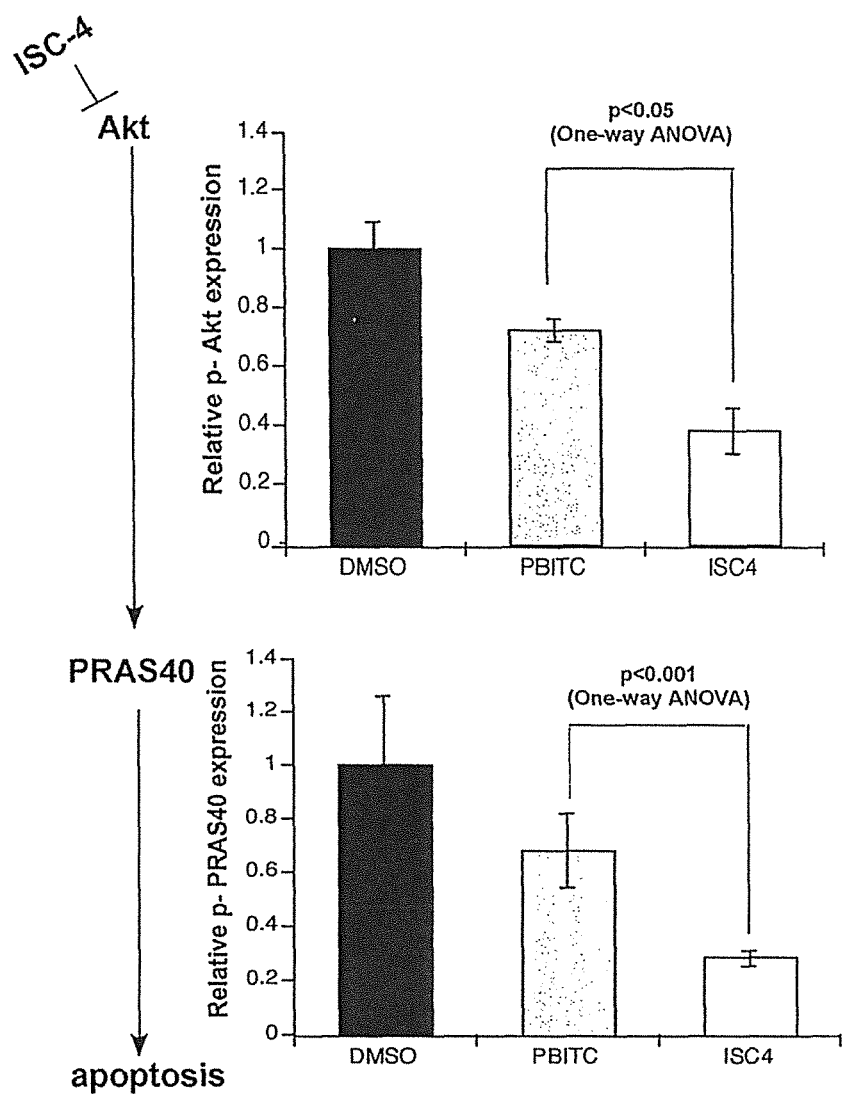
FIG. 11 is a bar graph showing quantitation of immunoblot analysis of tumor protein lysates from animals treated with DMSO, PBITC or ISC-4 and indicates decreased relative expression of phosphorylated (active) Akt and downstream PRAS40 of Akt3.

Western blot analysis of tumors harvested at day 13 from animals treated with DMSO, PBIT or ISC-4 showed significantly decreased expression of phosphorylated (active) Akt (p<0.05; One-way ANOVA) and downstream PRAS40 (p<0.001; One-way ANOVA) in ISC-4 tumor lysates compared to DMSO control or PBITC treated tumors. FIG. 11 illustrates a graph of quantitation of Western blot analysis of tumor protein lysates from animals treated with DMSO, PBITC or ISC-4 and indicates decreased relative expression of phosphorylated (active) Akt and downstream PRAS40 of Akt3. Thus, isoselenocyanates ISC-4 and ISC-6 more effectively inhibit the Akt3 signaling cascade in tumors at lower concentrations than corresponding sulfur containing isothiocyanates.

Example 24

Effects of inhibiting Akt3 signaling on melanoma tumorigenesis are shown using siRNA to inhibit Akt3 protein expression and thereby inhibit Akt3 activity.

Duplexed "Stealth" siRNA from Invitrogen (Carlsbad, Calif.) are: AKT3—GGA CUA UCU ACA UUC CGG AAA GAU U (SEQ ID NO. 1) and scrambled—AAU UCU CCG AAC GUG UCA CGU GAG A (SEQ ID NO. 2). Nucleofection using Amaxa Nucleofector (Koeln, Germany) is used to introduce siRNA into UACC 903 cells (Reagent R, program K17). SiRNA (100 pmoles) against Akt3 or scrambled siRNA are nucleofected into 1×10⁶ UACC 903 cells, which are then replated in DMEM supplemented with 10% FBS and allowed to recover for 1.5 days. Thirty-six hours later 1×10⁶ UACC 903 cells in 0.2 ml of DMEM supplemented with 10% FBS are injected subcutaneously into the left and right flanks of 4 to 6 week old nude mice. Control cells are nucleofected with scrambled siRNA or nucleofection buffer only. Dimensions of developing tumors are measured on alternate days using calipers up to day 17.5. siRNA-mediated inhibition of Akt3 signaling reduced the tumorigenic potential of melanoma cells.

Figure 12:
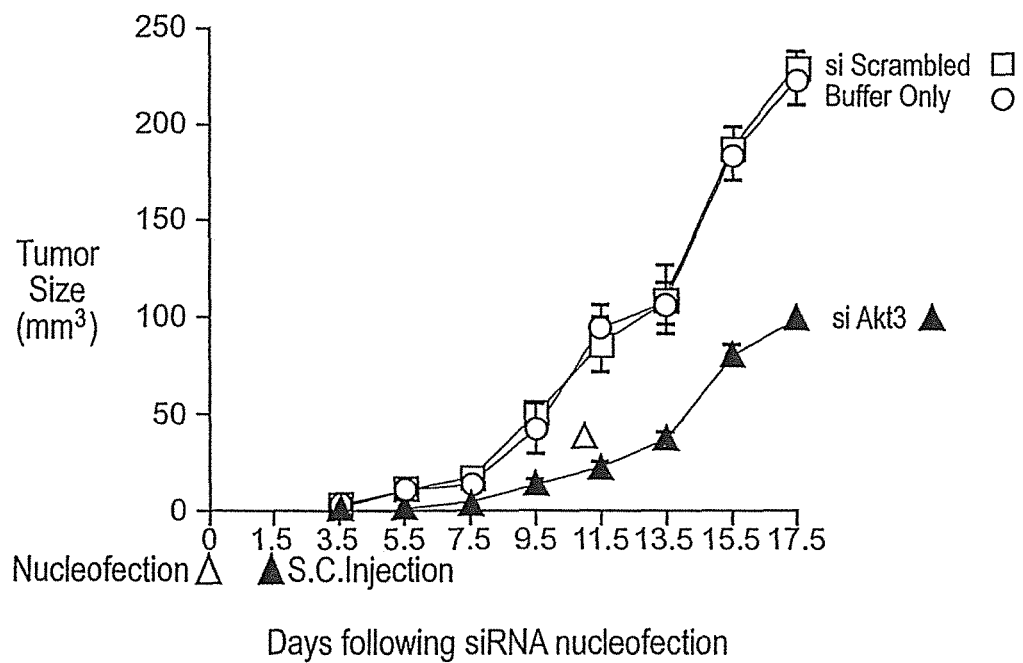
FIG. 12 is a line graph showing that decreased expression (activity) of Akt3 reduced the tumor size in animals injected with Akt3 siRNA treated cells compared to control cells nucleofected with scrambled siRNA or nucleofection buffer.

FIG. 12 is a graph showing that decreased expression (activity) of Akt3 reduced the tumor size in animals injected with Akt3 siRNA treated cells compared to control cells nucleofected with scrambled siRNA or nucleofection buffer. The tumorigenic potential of melanoma cells is decreased by ~60%. Thus, inhibition of Akt3 signaling led to significant melanoma tumor inhibition.

Figure 13:
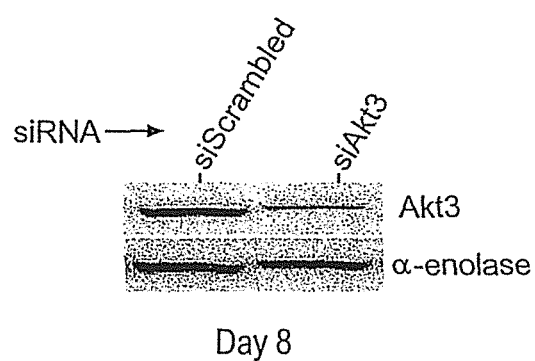
FIG. 13 is a reproduction of an image of an immunoblot analysis of tumor protein lysates showing reduction in expression of Akt3 in tumors by siRNA directed against Akt3.

FIG. 13 is a Western blot analysis of tumor protein lysates showing reduction in expression of Akt3, demonstrating effective knockdown of these proteins in tumors by siRNA directed against Akt3. α-enolase served as loading control. A tumor removed from animals 8 days after introduction of siRNA shows significantly less Akt3 protein than control tumors into which a scrambled siRNA had been introduced, demonstrating effective knockdown of Akt3 protein expression using this approach.

Example 25

Five million UACC903 cells are injected subcutaneously in a volume of 200 uL at each of two sites in nude mice to establish tumors. Six days following injection of the cells, mice are divided into four groups of five mice each. Mice in each group are injected i.p with 0.76 micromoles of sulforaphane (SFN), 0.76 micromoles (equivalent to 3 ppm selenium) of 1-isothiocyanto-4-methylselenobutane (SFN Iso Se Me), 0.76 micromoles (equivalent to 3 ppm selenium) of 1-isoselenocyanto-4-methylsulfinylbutane (SFN Iso Se) or DMSO (a vehicle control).

Figure 14A:
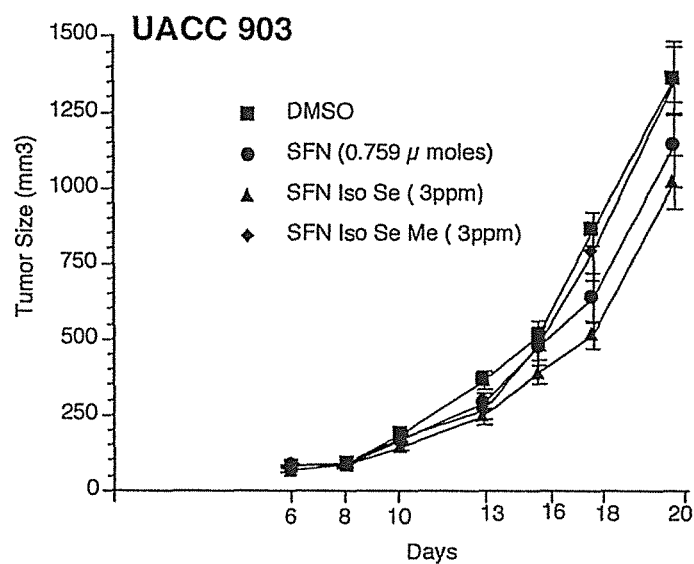
FIG. 14A is a line graph showing inhibition of tumor development by 1-isoselenocyanto-4-methylsulfinylbutane (SFN Iso Se, also interchangeably called ISC-SFN4 herein) compared to controls.
Figure 14B:
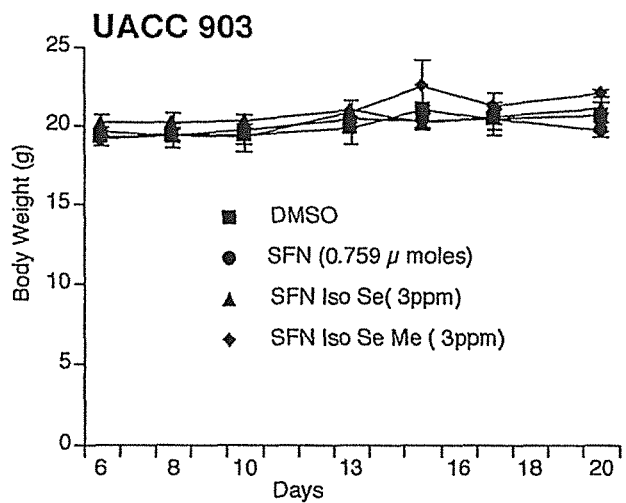
FIG. 14B is a line graph showing a lack of significant changes in body weight in treated animals, indicating that a lack of toxicity of the administered compounds.

FIG. 14A shows inhibition of tumor development by 1-isoselenocyanto-4-methylsulfinylbutane (SFN Iso Se) compared to controls. No toxicity of the administered compounds is apparent as indicated by lack of significant changes in body weight, shown in FIG. 14B.

$IC_{50}$ values for sulforaphane and 1-isoselenocyanto-4-methylsulfinylbutane (SFN Iso Se) are established in various cell lines. Results are shown in Table V.

TABLE V

| Cell type | IC-50 values | |
|---|---|---|
| | SFN | SFN Iso Se |
| A549 (lung) | 73 ± 3.6 | 35 ± 1.7 |
| UACC-903 (Melanoma) | 40 ± 0.89 | 17 ± 0.95 |
| 1205LU (Melanoma) | >50 | 39.2 ± 2 |
| CaCO2 (Colon Carcinoma) | 48 ± 5.9 | 16 ± 0.4 |
| MDA-MB231 (breast) | 57 ± 5 | 20 ± 0.46 |
| PC-3 (Prostate) | >50 | 24.8 ± 0.58 |
| HT1080 (Soft Tissue Sarcoma) | >50 | 25.59 ± 1.82 |
| IGROV-1 (ovarian carcinoma) | >50 | >50 |
| FF2441 (fibroblast cells) | >50 | >50 |

Example 26

Effect of ISC and ITC compounds on cell viability of prostate cancer cells LNCaP, PC-3 and DU-145.

Prostate cell lines, LnCaP, PC-3 and DU-145 are exposed to different concentrations, 5 micromolar, 10 micromolar or 25 micromolar, of ITCs including BITC, PEITC, PBITC, and PHITC, or ISCs, including ISC-1, ISC-2, ISC-4, and ISC-4, for 24 hours. Following incubation, cell viability is assayed using an MTS assay.

Example 27

Figure 15:
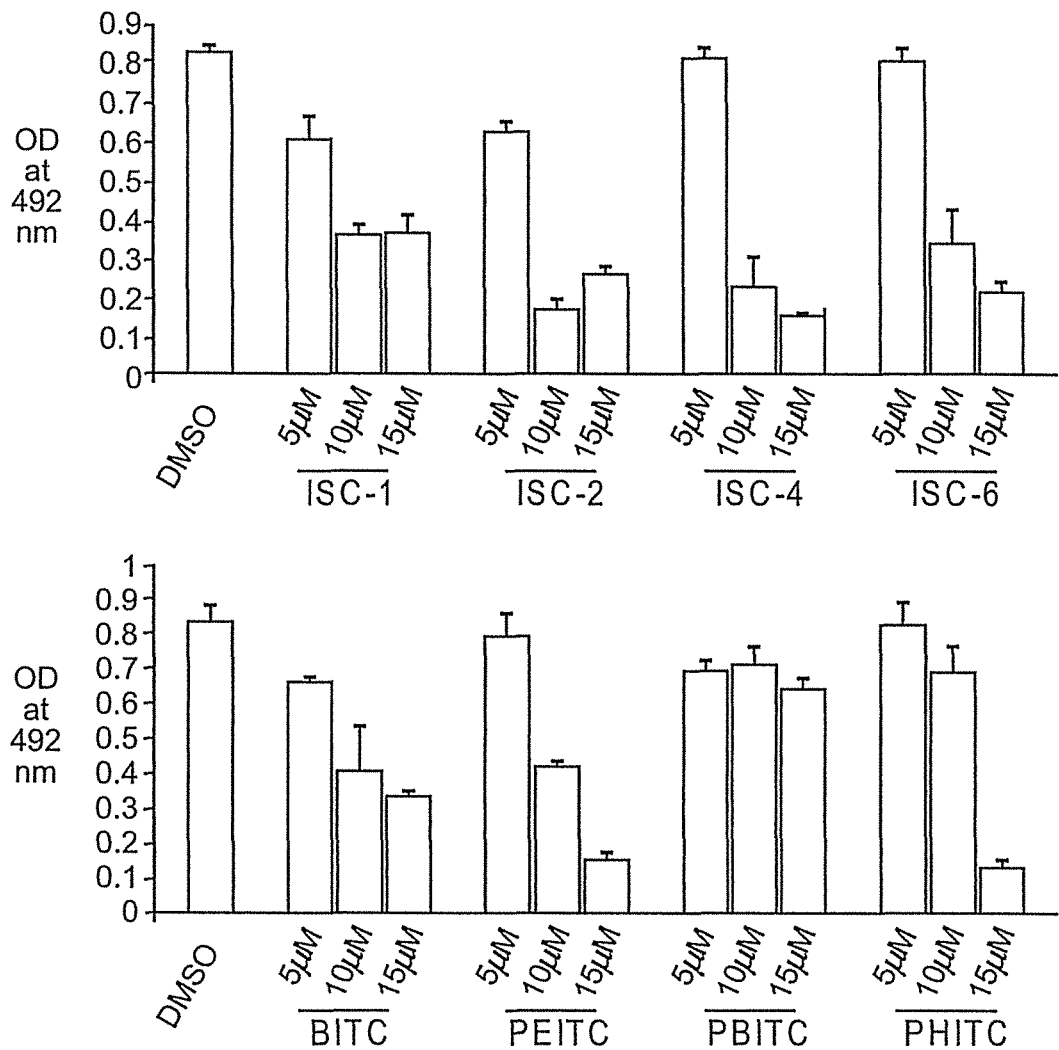
FIG. 15 is a bar graph showing results of a cell viability assay measuring inhibitory efficacy of DMSO, ISC-1, ISC-2, ISC-4, ISC-6, BITC, PEITC, PBITC, or PHITC on UACC 903 cells.

In vitro inhibitory efficacy of DMSO, ISC-1, ISC-2, ISC-4, ISC-6, BITC, PEITC, PBITC, or PHITC on UACC 903 cells is measured using the 3-(4,5-dimethylthiazol-2-yl)-5-(3-carboxymethoxyphenyl)-2-(4-sulfophenyl)-2H-tetrazolium (MTS) assay (Promega, Madison, Wis.). In brief, 2.5-5×10³ cells per well in 100 microliters DMEM containing 10% FBS are grown in a 96-well plate for 24 h and treated with either control DMSO vehicle or increasing concentrations (5-15 µM) of the tested isothiocyanate or isoselenocyanate for 24 hours. At this point cells are treated individually with either vehicle control DMSO or with increasing concentrations of ITC or ISC (2.5-100 µM) for 24 h. The percentages of viable cells compared to control DMSO treated cells are determined. FIG. 15 shows results of this assay.

Example 28

Figure 16:
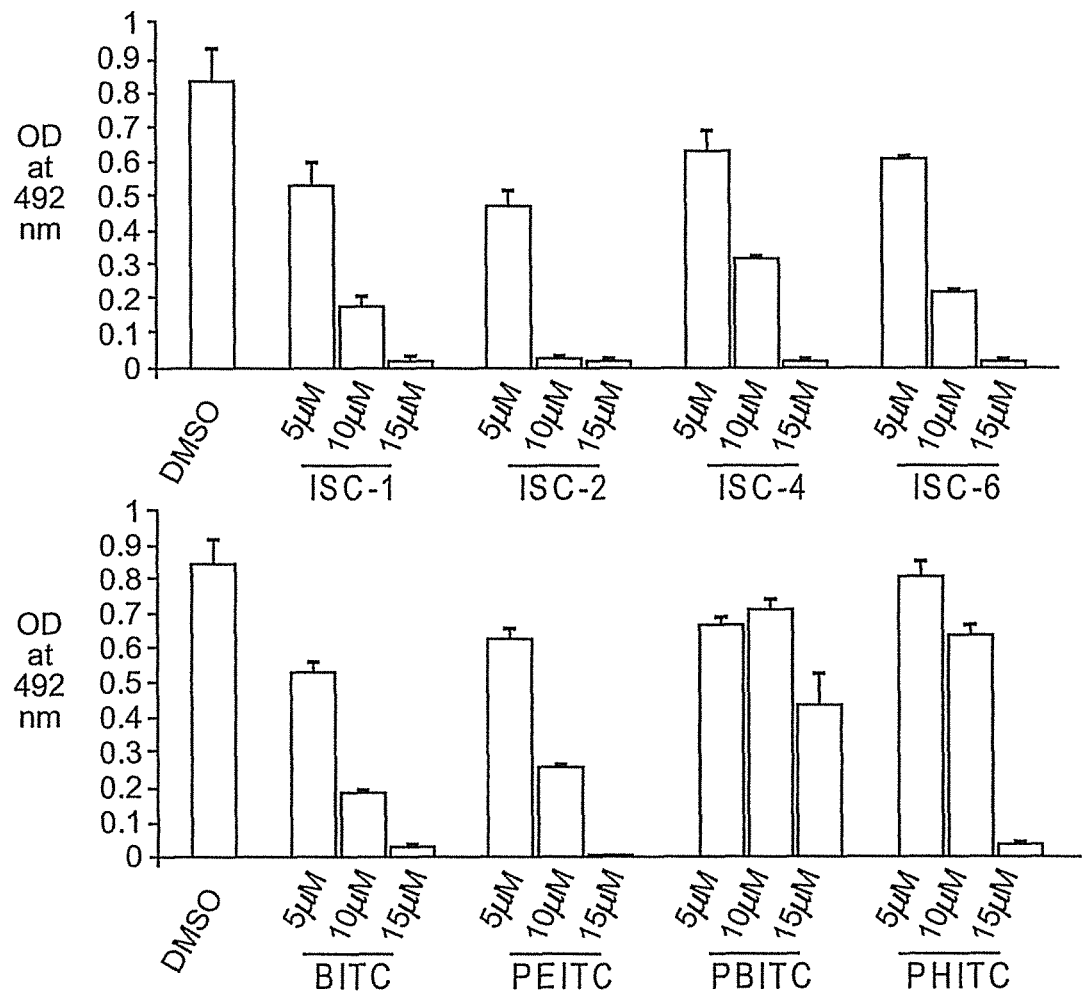
FIG. 16 is a bar graph showing the effect of DMSO or 5-15 μM of ISC-1, ISC-2, ISC-4, ISC-6, BITC, PEITC, PBITC, or PHITC on cell proliferation.

Cellular proliferation rate is measured by seeding 5×10³ human melanoma cell line UACC 903 cells in a 96-well plate, followed by treatment for 24 hours with DMSO or 5-15 of ISC-1, ISC-2, ISC-4, ISC-6, BITC, PEITC, PBITC, or PHITC for 24 hours. Proliferation rates are measured using a BrdU ELISA kit (Roche Applied Sciences, Indianapolis, Ind.). Results of this assay are shown in FIG. 16.

Example 29

Figure 17:
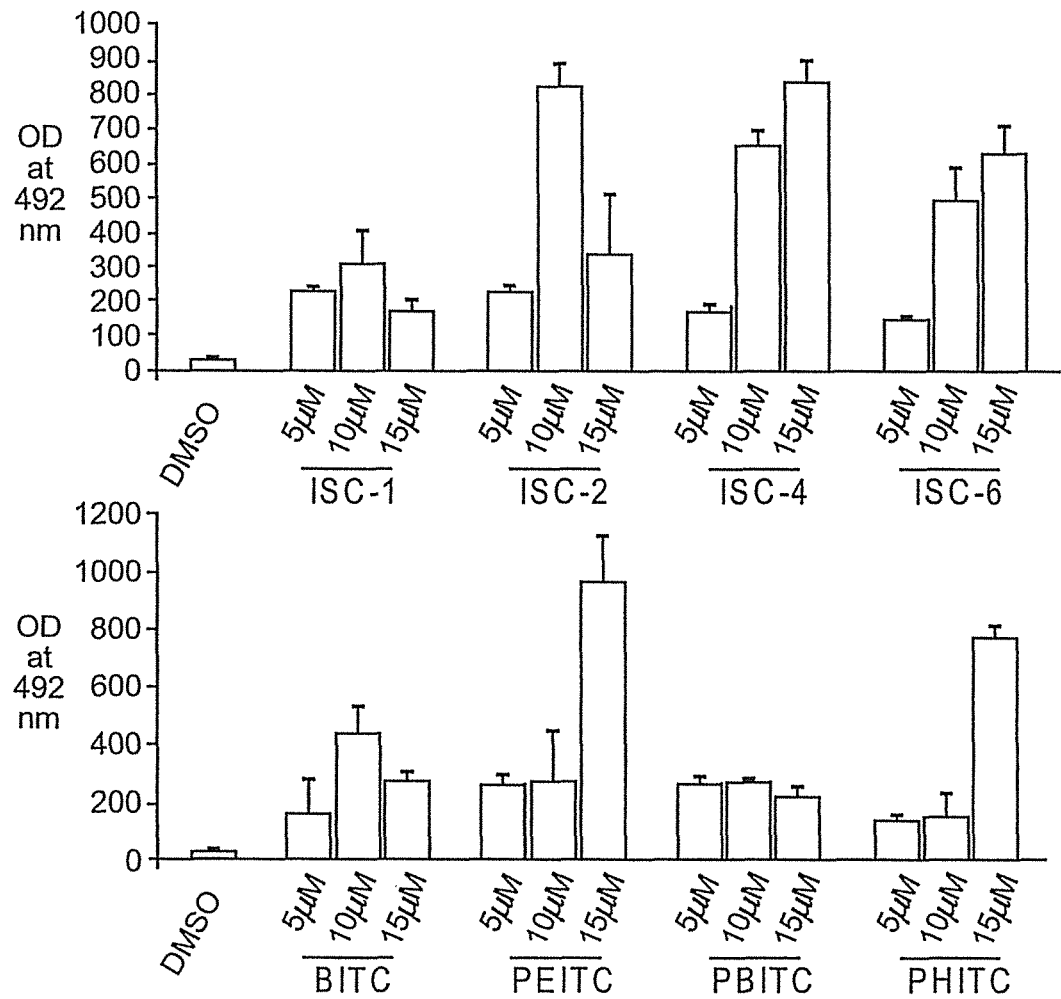
FIG. 17 is a bar graph showing the effect of DMSO or 5-15 μM of ISC-1, ISC-2, ISC-4, ISC-6, BITC, PEITC, PBITC, or PHITC on apoptosis.

Apoptosis rate is measured by seeding 5×10³ human melanoma cell line UACC 903 cells in a 96-well plate, followed by treatment for 24 hours with DMSO or 5-15 µM of ISC-1, ISC-2, ISC-4, ISC-6, BITC, PEITC, PBITC, or PHITC for 24 hours. Apoptosis rate is measured using an Apo-ONE Homogenous caspase-3/7 Assay kit (Promega Corporation, Madison, Wis.). Results of this assay are shown in FIG. 17.

Example 30

Tumorigenicity Assessment

Tumor kinetics are measured by subcutaneous injection of 5×10⁶ UACC 903 melanoma cells in 0.2 ml of DMEM supplemented with 10% FBS above both left and right rib cages of 4-6 week old female nude mice (Harlan Sprague Dawley, Indianapolis, Ind.). Six days later mice are randomly divided into control (DMSO) and experimental (ISC-1, ISC-2, ISC-4, ISC-6, BITC, PEITC, PBITC, PHITC) groups (5 mice/group; 2 tumors/mouse). Six days after subcutaneous injection of UACC 903 melanoma cells, mice are treated i. p. with BITC, PEITC, PBITC or PHITC (2.5 µmoles), or, ISC-1, ISC-2, ISC-4 or ISC-6 (0.76 µmoles, equivalent to 3 ppm selenium) thrice per week. (Monday, Wednesday and Friday). Control mice receive an equal volume of the vehicle, DMSO. The dimensions of the developing tumors (using calipers) and body weight are measured three times a week (Monday, Wednesday and Friday) and the size estimated in cubic millimeters.

Figure 18A:
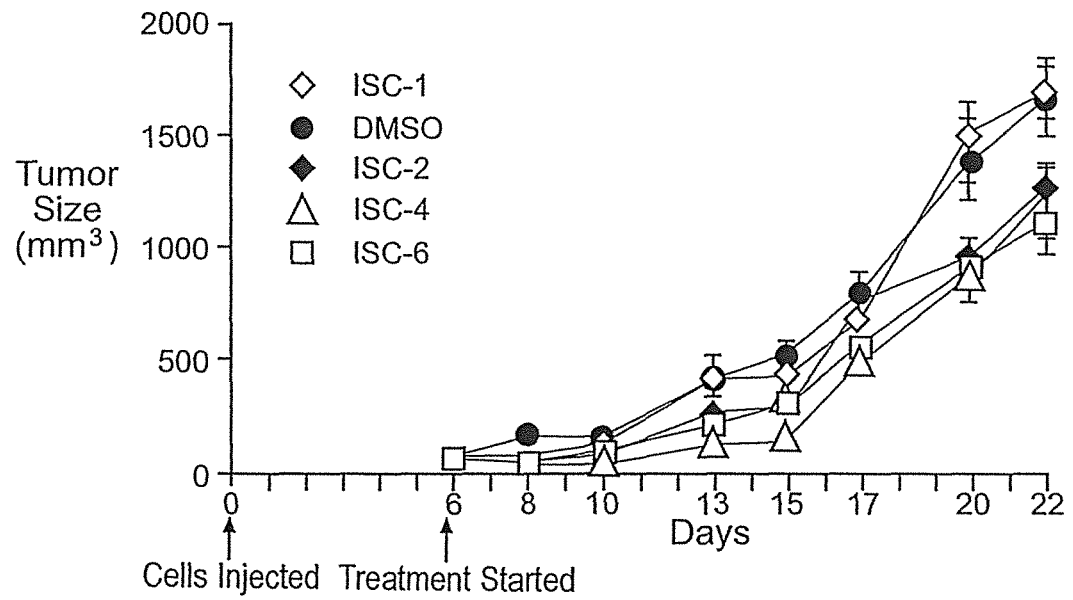
FIG. 18A is a line graph showing effect of selected isoselenocyanates on tumor size.
Figure 18B:
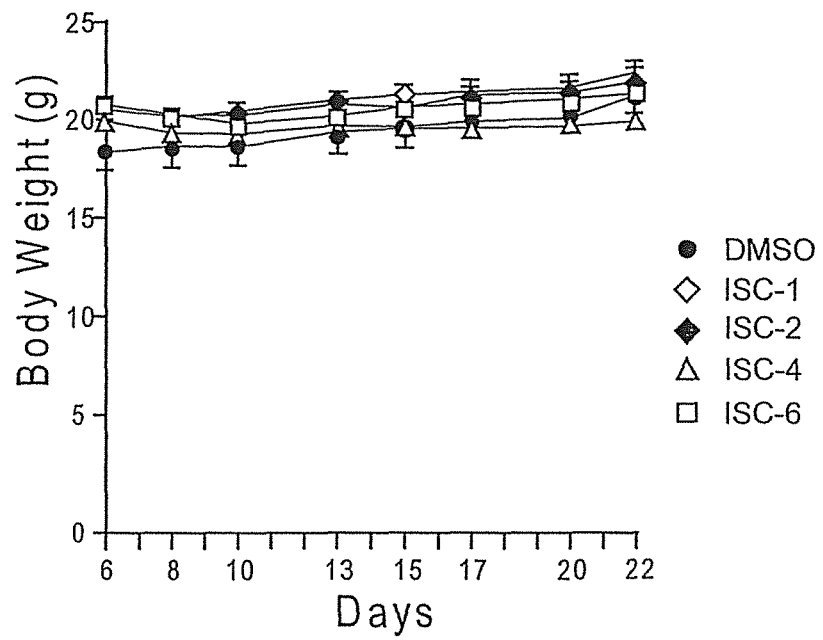
FIG. 18B is a line graph showing effect of selected isoselenocyanates on body weight.
Figure 18C:
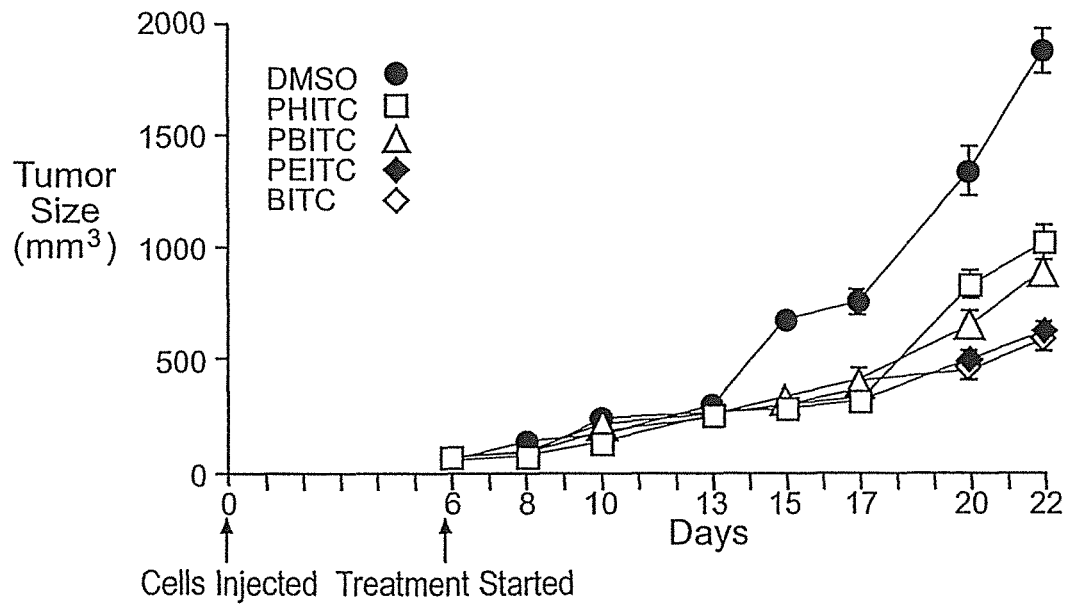
FIG. 18C is a line graph showing effect of selected isothiocyanates on tumor size.
Figure 18D:
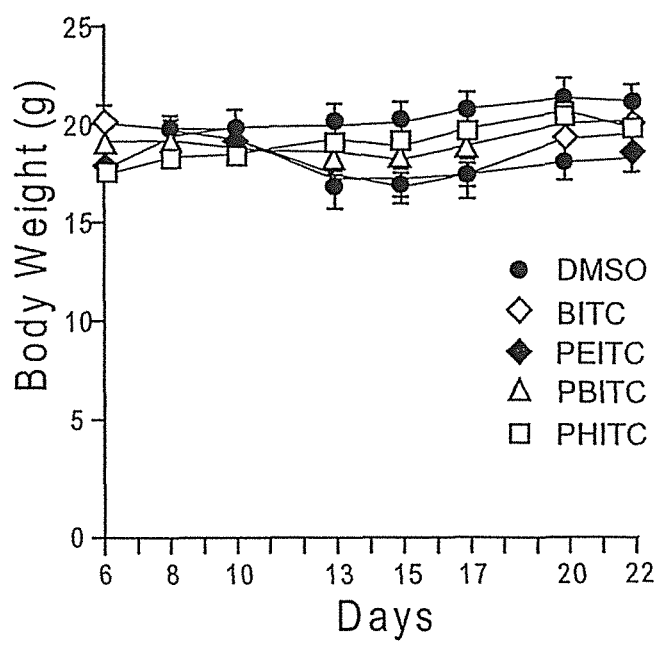
FIG. 18D is a line graph showing effect of selected isothiocyanates on body weight.

At a dose of 0.76 µmoles, ISC-2 to ISC-6 showed about 30-45% reduction in tumor size with the effect increasing with the increasing alkyl chain length from ISC-2 to ISC-6 (FIG. 18A). ISC-1 failed to show any effect at this concentration. There was no related toxicity observed at this dose for any of the ISC derivatives. ITC derivatives are also effective in reducing the tumor size at a dosage of 2.5 micromoles, ~3 times higher than the administered dosage of ISC compounds, shown in FIG. 18C. A reverse trend of chain length effect is observed, with BITC being the most effective. FIGS. 18B and 18D shows the body weights of test compound treated mice treated compared to the control DMSO vehicle treated mice. No significant difference in weights is detected between groups, demonstrating negligible toxicity.

Example 31

Western Blotting, Immunoprecipitation, and Kinase Assay for Akt1, Akt2 and Akt3

Dysregulation of Akt1, Akt2 and/or Akt3 can be observed in cells using various well-known techniques Western blot procedure for detection of Akt1, Akt2 and/or Akt3 dysregulation is performed according to standard procedures, for instance as described herein and in Harlow, E. and Lane, D., Antibodies: A Laboratory Manual, Cold Spring Harbor Laboratory Press, 1988; J. D. Pound (Ed.) Immunochemical Protocols, Methods in Molecular Biology, Humana Press; 2nd ed., 1998; Stahl, J. M., et al., Cancer Res., 63:2881-2890, 2003; and Stahl, J. M., et al., Cancer Res., 64:7002-7010, 2004.

Immunoprecipitation for detection of Akt1, Akt2 and/or Akt3 dysregulation is performed according to standard procedures, for instance as described herein and in Harlow, E. and Lane, D., Antibodies: A Laboratory Manual, Cold Spring Harbor Laboratory Press, 1988; J. D. Pound (Ed.) Immunochemical Protocols, Methods in Molecular Biology, Humana Press; 2nd ed., 1998; Stahl, J. M., et al., Cancer Res., 63:2881-2890, 2003; and Stahl, J. M., et al., Cancer Res., 64:7002-7010, 2004. For example, briefly described, protein is collected from cells after addition of protein lysis buffer [50 mmol/L Tris-HCl (pH 7.5), 0.1% Triton X-100, 1 mmol/L EDTA, 1 mmol/L EGTA, 50 mmol/L NaFl, 10 mmol/L sodium β-glycerol phosphate, 5 mmol/L sodium inorganic pyrophosphate, 1 mmol/L sodium orthovanadate, 0.1% 2-mercaptoethanol, and 0.5% protease inhibitor mixture (Sigma, St. Louis, Mo.)] to a sample, such as plates of cells or biopsy material, followed by snap freezing in liquid nitrogen. Cellular debris is pelleted by centrifugation (10,000×g) of lysates, and protein concentration is quantitated using the Bio-Rad Protein Assay (Bio-Rad, Hercules, Calif.). Protein for immunoprecipitation (100 µg) is incubated with 2 µg of Akt1 or Akt2 or 5 µL, of Akt3 antibody overnight at 4° C. with constant mixing. A no antigen negative control is prepared by adding antibody to the lysis buffer only. Next, 15 µL of equilibrated GammaBind G Sepharose beads (Amersham Biosciences, Piscataway, N.J.) is added to each tube and incubated for 2 hours (4° C.) with constant mixing. Pelleted beads are washed twice with lysis buffer to remove unbound antibody and protein. Samples are then electrophoresed under reducing conditions according to the protocol provided by Invitrogen Life Technologies, Inc. (Carlsbad, Calif.) with the NuPage Gel System. Western blots of the electrophoresed samples are probed with an anti-phospho-Akt (Ser-473) antibody and quantitated by densitometry as described in Stahl, J. M., et al., Cancer Res., 63:2881-2890, 2003.

Antibodies for use in immunoassays for Akt1, Akt2 and/or Akt3 can be obtained commercially, for instance an Akt1 antibody is available from Cell Signaling Technologies, Beverly, Mass., an Akt2 antibody is available from Santa Cruz Biotechnology, Santa Cruz, Calif. and an Akt3 antibody is available from Upstate Biotechnology, Lake Placid, N.Y. An anti-phospho-Akt (Ser-473) antibodies can also be obtained commercially, e.g. from Cell Signaling Technologies, Beverly, Mass. Anti-Akt1, Akt2 and/or Akt3 antibodies can also be produced by well-known techniques such as described, for instance, in Harlow, E. and Lane, D., Antibodies: A Laboratory Manual, Cold Spring Harbor Laboratory Press, 1988.

Akt kinase assays are performed according to standard kinase assay procedures. Briefly described, 15 µL of equilibrated GammaBind G Sepharose beads are incubated with 2 µg of Akt1 or Akt2 antibody, or 5 µL of Akt3 antibody in a volume of 350 µL of lysis buffer at 4° C. with constant mixing for 2 hours. Microcystin (1 µmol/L) from MP Biomedicals (Irvine, Calif.) is added to the lysis buffer to ensure complete inactivation of cellular PP1 and PP2 phosphatases. The antibody/Sepharose complex is washed twice with 750 µL of lysis buffer and then incubated with 100 µg of protein in a volume of 350 µL overnight at 4° C. with constant mixing. This complex is washed with 500 µL of lysis buffer (3×) and then once with 500 µL of assay dilution buffer [20 mmol/L 4-morpholinepropanesulfonic acid (pH 7.2), 25 mmol/L β-glycerol phosphate, 1 mmol/L sodium orthovanadate, and 1 mmol/L dithiothreitol]. Protein kinase A (PKA) inhibitor peptide (10 mol/L) from Santa Cruz Biotechnology (Santa Cruz, Calif.), 37.5 µmol/L ATP, 17 mmol/L MgCl2, 0.25 µCi/µL [gamma-$^{32}$P]ATP, and 90 µmol/L Akt-specific substrate Crosstide from Upstate Biotechnology (Lake Placid, N.Y.) are added to the tubes in assay dilution buffer and incubated at 35° C. for 10 minutes with continuous mixing. Next, 20 µL of liquid are transferred to phosphocellulose paper, which is washed three times for 5 minutes with 40 mL of 0.75% phosphoric acid. After a 5-minute acetone wash, the phosphocellulose was allowed to dry and transferred to a scintillation vial with 5 mL of Amersham Biosciences scintillation fluid, and counts per minute were measured in a Beckman Coulter LS 3801 Liquid Scintillation System (Fullerton, Calif.).

Detection of Dysregulated Akt in Human Material

Formalin-fixed paraffin-embedded melanoma specimens are used for immunohistochemistry to measure phosphorylated Akt. A phospho-Akt (Ser-473) monoclonal antibody, Cell Signaling Technologies, is used at a 1:50 titer according to the manufacturer's recommended protocol. Specificity and intensity of staining are determined through qualitative comparison with internal blood vessel endothelium, squamous epithelium, or smooth muscle controls present in each specimen.

Example 32

ISC-4 more efficiently inhibits melanoma cell growth compared to normal human fibroblast cells. 10×10$^3$ normal human fibroblasts (FF2441) expressing Akt3 at normal levels and 5×10$^3$ metastatic melanoma cells (UACC 903) having activated Akt3 are plated in 96 well plates in 100 µL DMEM containing 10% FBS and grown for 24 hours respectively. Exponentially growing cells are treated with increasing concentrations (2.5-100 µM) of ISC-4 for 24 hours and IC$_{50}$ (µM) values determined.

Sensitivity of melanoma cells to ISC-4 with elevated Akt3 signaling is compared to fibroblast cells with normal levels of Akt activity. Three-fold higher drug concentration of ISC-4 (37.5 µM) is required to kill fibroblasts with normal levels of Akt activity compared to melanoma cells (12±3 µM) with elevated Akt activity. Thus, cancer cells with constitutively active Akt signaling are 3-fold more sensitive to ISC-4 than normal cells with regular Akt activity. These results show that ISC-4 more effectively kill cells having increased Akt activity than those having normal levels.

Example 33

Effect of topical ISC-4 application on melanoma tumor growth—in vitro (Skin Reconstructs). FIG. 19 is a bar graph showing the effects of topically applied PBITC or ISC-4 on reconstructed human skin containing GFP tagged UACC 903 human melanoma cells.

Generation of skin containing melanocytic lesions is briefly described. To create skin in a culture dish, human fibroblasts, were trypsinized and resuspended in 10% reconstitution buffer, 10% 10×DMEM (Mediatech, Herndon, Va.), 2.4 microliters/ml of 10 M NaOH, and 80% collagen I (BD Discovery Labware Inc., Bedford, Mass.) at a concentration of 2.5×10$^5$ cells/ml on ice (Ozbun M A, Meyers C. J Virol 1996, 70: 5437-46.). Mixture was then aliquoted into 6 or 12 well plates and incubated at 37° C. for 3 hours. E-media was added to each well to equilibrate the dermal matrix (Wu Y J, Parker L M, Binder N E, et al., Cell 1982, 31: 693-703.). After two days of growth, keratinocytes and melanoma cells (WM35-GFP or UACC 903-GFP) were trypsinized and resuspended at a 1:10 ratio of melanoma cells (nucleofected or untreated) to keratinocytes in E-media. One milliliter of cell suspension added to each well on top of the dermal layer. Following two days growth, reconstructed skin was transferred onto wire grids and fed via diffusion from E-media below the platforms.

Reconstructed human skin containing GFP tagged UACC 903 human melanoma cells were treated with 12.5 and 25 µM PBITC or ISC-4 and the tumor area occupied measured using fluorescence microscopy.

The result shows an ~80% decrease in tumor area occupied by melanoma cells upon ISC-4 treatment compared to control DMSO treated or untreated skins. Similar results are observed with other melanoma cell lines.

Example 34

Effect of Topical ISC-4 Application on Melanoma Tumor Growth—In Vivo

Chemopreventive or chemotherapeutic effect of ISC-4 on cutaneous tumor development is measured by subcutaneous injection of 1 million UACC 903 cells in 0.2 ml of DMEM—10% FBS above both the left and right rib cages of 4- to 6-week old female athymic nude mice using 24 g needles. 24 hours later, animals are treated daily with ISC-4 (0.063-0.19 mmoles equivalent to 0.25-0.75 ppm), PBITC (0.063-0.19 mmoles) or vehicle control (acetone) for 3-4 weeks. The dimensions of the developing tumors are measured alternate days using calipers and the sizes estimated in cubic millimeters. A minimum of 5 mice per group is used for the topical treatment.

FIG. 20 shows a pair of line graphs showing the effect of topical ISC-4 application on melanoma tumor growth in vivo. Topical treatment with (0.063-0.19 µmoles equivalent to 0.25-0.75 ppm) ISC-4 leads to decreased tumor size compared to vehicle control (as shown in the upper graph in FIG. 20) or PBITC (0.063-0.19 μmoles) with no systemic toxicity (as shown by body weight measurements in the lower graph in FIG. 20).

Example 35

Effect of Topical ISC-4 Application on Melanoma Tumor Growth—In Vivo

Chemopreventive or chemotherapeutic effect of ISC-4 on cutaneous tumor development is measured by subcutaneous injection of 1 million UACC 903 cells in 0.2 ml of DMEM— 10% FBS above both the left and right rib cages of 4- to 6-week old female athymic nude mice using 24 g needles. 24 hours later, animals were treated daily with ISC-4 (12.5-50 μM), PBITC (12.5-50 μM), or vehicle control (acetone) for 3-4 weeks. The dimensions of the developing tumors are measured alternate days using calipers and the sizes estimated in cubic millimeters. A minimum of 5 mice per group was used for the topical treatment.

Figure 21:
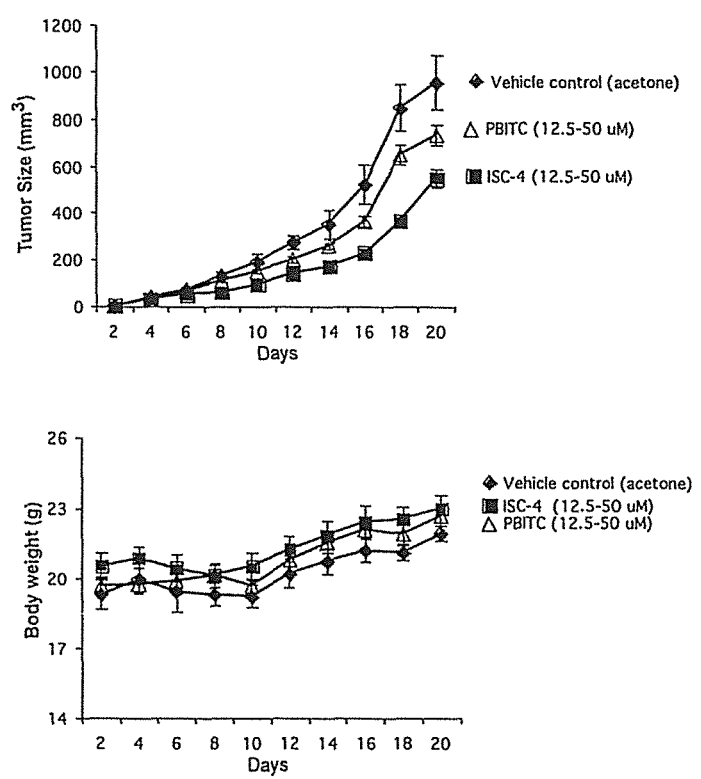
FIG. 21 is a pair of line graphs showing the effect of topical ISC-4 application on melanoma tumor growth in vivo.

Topical treatment with ISC-4 (12.5-50 μM) significantly reduces melanoma tumor development by ~50% compared to PBITC (12.5-50 μM) (as shown in the upper graph in FIG. 21) or vehicle control with no systemic toxicity (as shown by body weight measurements in the lower graph in FIG. 21).

REFERENCES

Serrone L, Hersey P. The chemoresistance of human malignant melanoma: an update. Melanoma Research 1999; 9:51-8.

Grossman D, Altieri D C. Drug resistance in melanoma: mechanisms, apoptosis, and new potential therapeutic targets. Cancer & Metastasis Reviews 2001; 20:3-11.

Helmbach H, Rossmann E, Kern M A, Schadendorf D. Drug-resistance in human melanoma. International Journal of Cancer 2001; 93:617-22.

Markovic S N, Erickson L A, Rao R D, et al. Malignant melanoma in the 21st century, part 1: epidemiology, risk factors, screening, prevention, and diagnosis. Mayo Clin Proc 2007; 82:364-80.

Jemal A, Thomas A, Murray T, Thun M. Cancer statistics, 2002. [comment][erratum appears in CA Cancer J Clin 2002 March-April; 52(2):119]. Ca: a Cancer Journal for Clinicians 2002; 52:23-47.

Amiri K I, Horton L W, LaFleur B J, Sosman J A, Richmond A. Augmenting chemosensitivity of malignant melanoma tumors via proteasome inhibition: implication for bortezomib (VELCADE, PS-341) as a therapeutic agent for malignant melanoma. Cancer Res 2004; 64:4912-8.

Gray-Schopfer V, Wellbrock C, Marais R. Melanoma biology and new targeted therapy. Nature 2007; 445:851-7.

Brazil D P, Hemmings B A. Ten years of protein kinase B signalling: a hard Akt to follow. Trends Biochem Sci 2001; 26:657-64.

Nicholson K M, Anderson N G. The protein kinase B/Akt signalling pathway in human malignancy. Cell Signal 2002; 14:381-95.

Stahl J M, Sharma A, Cheung M, et al. Deregulated Akt3 activity promotes development of malignant melanoma. Cancer Res 2004; 64:7002-10.

Stahl J M, Cheung M, Sharma A, Trivedi N R, Shanmugam S, Robertson G P. Loss of PTEN promotes tumor development in malignant melanoma. Cancer Res 2003; 63:2881-90.

Madhunapantula S V, Sharma A, Robertson G P. PRAS40 deregulates apoptosis in malignant melanoma. Cancer Res 2007; 67:3626-36.

Keum Y S, Jeong W S, Kong A N. Chemoprevention by isothiocyanates and their underlying molecular signaling mechanisms. Mutat Res 2004; 555:191-202.

Zhang Y. Cancer-preventive isothiocyanates: measurement of human exposure and mechanism of action. Mutat Res 2004; 555:173-90.

Zhang Y, Kensler T W, Cho C G, Posner G H, Talalay P. Anticarcinogenic activities of sulforaphane and structurally related synthetic norbornyl isothiocyanates. Proc Natl Acad Sci USA 1994; 91:3147-50.

Hecht S S. Chemoprevention by isothiocyanates. J Cell Biochem Suppl 1995; 22:195-209.

Zhang Y, Yao S, Li J. Vegetable-derived isothiocyanates: antiproliferative activity and mechanism of action. Proc Nutr Soc 2006; 65:68-75.

Ji Y, Kuo Y, Morris M E. Pharmacokinetics of dietary phenethyl isothiocyanate in rats. Pharm Res 2005; 22:1658-66.

El-Bayoumy K, Sinha R, Pinto J T, Rivlin R S. Cancer chemoprevention by garlic and garlic-containing sulfur and selenium compounds. J Nutr 2006; 136:864 S-9S.

Miyoshi N, Uchida K, Osawa T, Nakamura Y. A link between benzyl isothiocyanate-induced cell cycle arrest and apoptosis: involvement of mitogen-activated protein kinases in the Bcl-2 phosphorylation. Cancer Res 2004; 64:2134-42.

Chiao J W, Wu H, Ramaswamy G, et al. Ingestion of an isothiocyanate metabolite from cruciferous vegetables inhibits growth of human prostate cancer cell xenografts by apoptosis and cell cycle arrest. Carcinogenesis 2004; 25:1403-8.

Reinhold U, Biltz H, Bayer W, Schmidt K H. Serum selenium levels in patients with malignant melanoma. Acta Derm Venereol 1989; 69:132-6.

Bandura L, Drukala J, Wolnicka-Glubisz A, Bjornstedt M, Korohoda W. Differential effects of selenite and selenate on human melanocytes, keratinocytes, and melanoma cells. Biochem Cell Biol 2005; 83:196-211.

Brigelius-Flohe R. Selenium compounds and selenoproteins in cancer. Chem Biodivers 2008; 5:389-95.

Unni E, Koul D, Yung W K, Sinha R. Se-methylselenocysteine inhibits phosphatidylinositol 3-kinase activity of mouse mammary epithelial tumor cells in vitro. Breast Cancer Res 2005; 7:R699-707.

Hu H, Jiang C, Li G, Lu J. PKB/AKT and ERK regulation of caspase-mediated apoptosis by methylseleninic acid in LNCaP prostate cancer cells. Carcinogenesis 2005; 26:1374-81.

Krishan A. Rapid flow cytofluorometric analysis of mammalian cell cycle by propidium iodide staining. J Cell Biol 1975; 66:188-93.

Yang L, Dan H C, Sun M, et al. Akt/protein kinase B signaling inhibitor-2, a selective small molecule inhibitor of Akt signaling with antitumor activity in cancer cells overexpressing Akt. Cancer Res 2004; 64:4394-9.

Feun L G, Blessing J A, Barrett R J, Hanjani P. A phase II trial of tricyclic nucleoside phosphate in patients with advanced squamous cell carcinoma of the cervix. A Gynecologic Oncology Group Study. Am J Clin Oncol 1993; 16:506-8.

Karst A M, Dai D L, Cheng J Q, Li G. Role of p53 up-regulated modulator of apoptosis and phosphorylated. Akt in melanoma cell growth, apoptosis, and patient survival. Cancer Res 2006; 66:9221-6.

Any patents or publications mentioned in this specification are incorporated herein by reference to the same extent as if each individual publication is specifically and individually indicated to be incorporated by reference. Pending U.S. patent application Ser. No. 12/102,629 and U.S. Provisional Patent Application Ser. Nos. 60/911,565, filed Apr. 13, 2007 and 60/959,554, filed Jul. 13, 2007, are all incorporated herein by reference in their entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a subject having melanoma, comprising:
    administering a therapeutically effective amount of a composition comprising a compound having the structural formula:
    R—(CH$_2$)$_n$—N=C=X, where n is an integer in the range of 1-8, inclusive, where X is Se, and where R is phenyl to the subject having melanoma.

2. The method of claim 1, wherein the composition comprises a phenylalkyl isoselenocyanate having the structural formula:

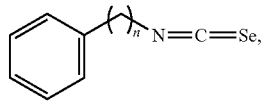

where n is 4 or 6.

3. The method of claim 1 wherein the subject is human.

4. The method of claim 1 wherein the composition is formulated for topical application.

5. The method of claim 1, wherein the cancer is characterized by dysregulation of Akt.

6. The method of claim 1, wherein the cancer is characterized by dysregulation of Akt3.

7. The method of claim 1, wherein administering the therapeutically effective amount of the composition to a subject detectably increases apoptosis and/or decreases proliferation of cells of the melanoma.

8. The method of claim 1, further comprising administration of an adjunct anti-cancer treatment.

* * * * *